United States Patent
Netravali et al.

(10) Patent No.: US 12,303,216 B2
(45) Date of Patent: May 20, 2025

(54) SURGICAL TRACKING METHODS AND FIBER OPTIC SHAPE SENSING DEVICES THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Nathan Anil Netravali, Littleton, MA (US); Paul Alexander Torrie, Marblehead, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/582,187

(22) Filed: Feb. 20, 2024

(65) Prior Publication Data
US 2024/0225753 A1 Jul. 11, 2024

Related U.S. Application Data

(63) Continuation of application No. 17/242,501, filed on Apr. 28, 2021, now Pat. No. 11,974,818.
(Continued)

(51) Int. Cl.
*A61B 34/20* (2016.01)
*A61B 17/17* (2006.01)
(Continued)

(52) U.S. Cl.
CPC .............. *A61B 34/20* (2016.02); *A61B 17/17* (2013.01); *A61B 17/3403* (2013.01);
(Continued)

(58) Field of Classification Search
CPC ......... A61B 34/30; A61B 34/20; A61B 90/03; A61B 17/17; A61B 17/3403;
(Continued)

(56) References Cited

U.S. PATENT DOCUMENTS 8,050,523 B2 * 11/2011 Younge ................ A61B 5/6852
385/13
8,746,076 B2 * 6/2014 Rogge ...................... G01L 1/24
385/12
(Continued)

*Primary Examiner* — Kevin T Truong
*Assistant Examiner* — Diana Jones

(57) ABSTRACT

Methods, non-transitory computer readable media, surgical tracking devices, and systems that facilitate improved tracking in surgical environments are disclosed. With this technology, a fiber optic shape sensing (FOSS) device is rigidly attached to patient anatomy and/or surgical instrument(s) to facilitate location and/or flexibility tracking. The data provided by the FOSS device can be analyzed and registered to preoperative or intraoperative 3D anatomy model(s). The FOSS device can be attached to a surgical instrument to provide intraoperative guidance, used to locate a hollow needle for tracking bones in a minimally invasive manner, and/or used to detect bending in an instrument such as an arthroscope or tissue removing burr shaft, for example. The tracked location and/or flexibility data provided by the FOSS device can also be used to automatically control the location and/or operation of a surgical instrument during a surgical proceeding to facilitate improved surgical accuracy and patient outcomes.

16 Claims, 21 Drawing Sheets

Related U.S. Application Data

(60) Provisional application No. 63/016,370, filed on Apr. 28, 2020.

(51) Int. Cl.
  *A61B 17/34*   (2006.01)
  *A61B 17/56*   (2006.01)
  *A61B 34/30*   (2016.01)
  *A61B 90/00*   (2016.01)

(52) U.S. Cl.
  CPC .......... *A61B 17/3472* (2013.01); *A61B 34/30* (2016.02); *A61B 90/03* (2016.02); *A61B 2017/564* (2013.01); *A61B 2034/2061* (2016.02); *A61B 2090/373* (2016.02)

(58) Field of Classification Search
  CPC ........ A61B 17/3472; A61B 2034/2061; A61B 2090/373; A61B 2017/564
  USPC .......................................................... 606/96
  See application file for complete search history.

(56) References Cited

U.S. PATENT DOCUMENTS

| | | | |
|---|---|---|---|
| 10,405,908 B2* | 9/2019 | Redmond | A61B 17/8863 |
| 10,638,953 B2* | 5/2020 | Duindam | A61B 17/3209 |
| 2011/0113852 A1* | 5/2011 | Prisco | A61B 34/30 |
| | | | 385/13 |
| 2013/0204124 A1* | 8/2013 | Duindam | A61B 17/3468 |
| | | | 604/272 |
| 2016/0206384 A1 | 7/2016 | Dimaio et al. | |
| 2016/0228199 A1* | 8/2016 | Flexman | G02B 23/2469 |
| 2017/0209071 A1 | 7/2017 | Zhao et al. | |
| 2017/0273542 A1 | 9/2017 | Au | |
| 2018/0235709 A1 | 8/2018 | Donhowe et al. | |
| 2019/0192234 A1 | 6/2019 | Gadda et al. | |
| 2019/0269470 A1 | 9/2019 | Barbagli et al. | |

\* cited by examiner

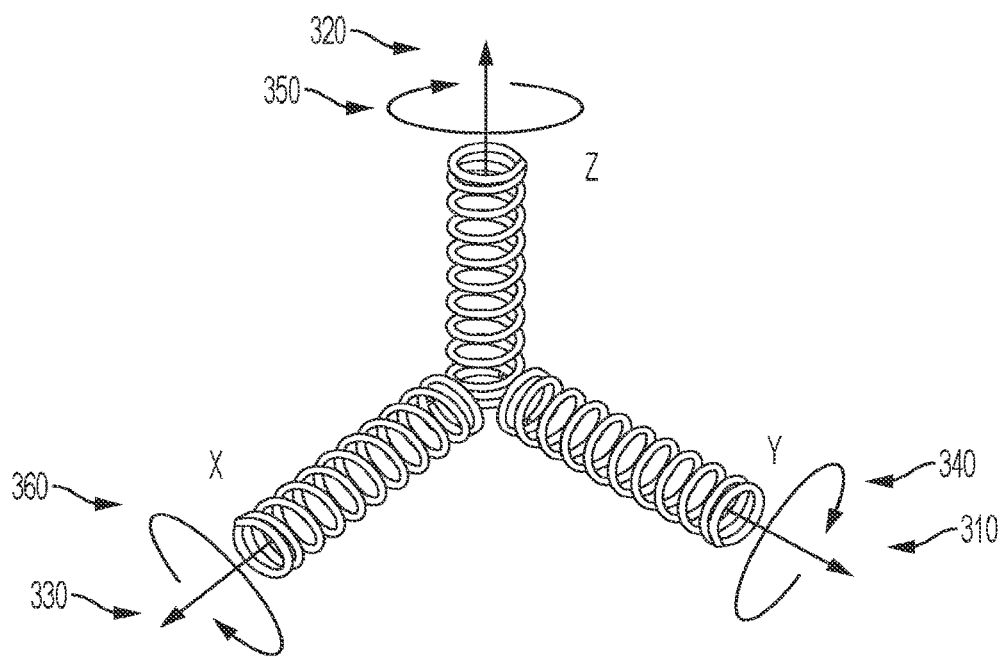
FIG. 3A
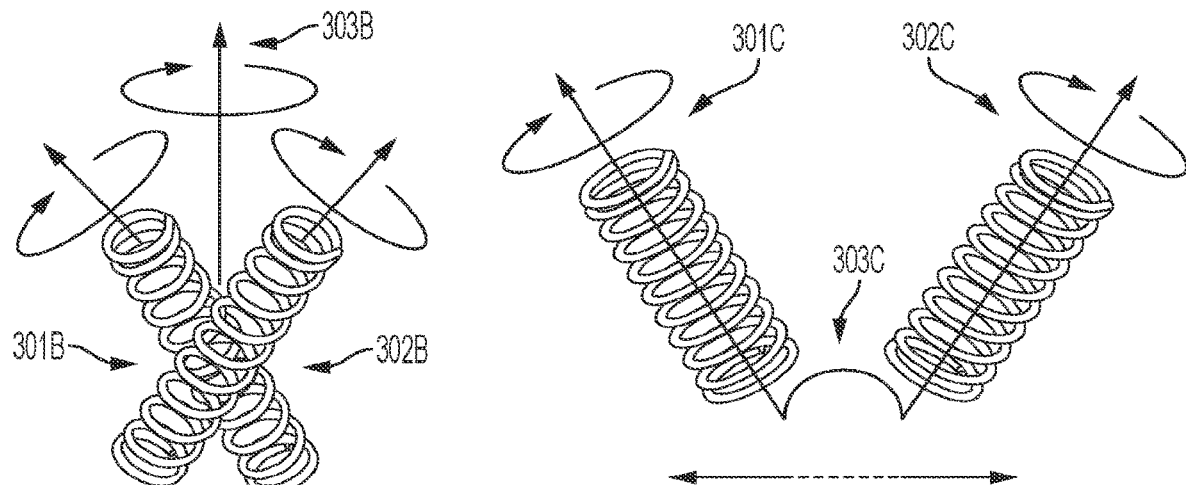
FIG. 3B
FIG. 3C

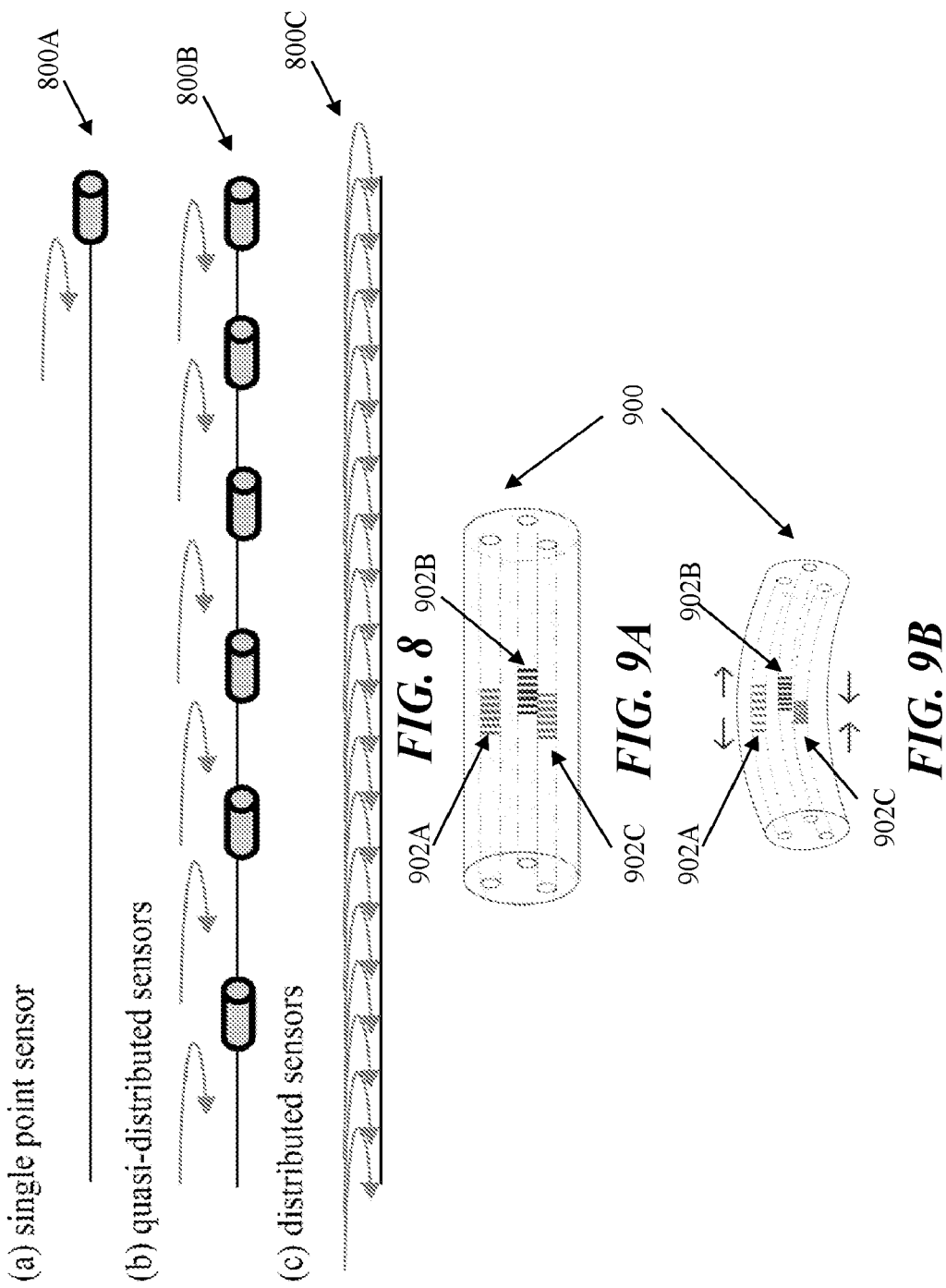

SURGICAL TRACKING METHODS AND FIBER OPTIC SHAPE SENSING DEVICES THEREOF

This application is a continuation of U.S. application Ser. No. 17/242,501 filed Apr. 28, 2021 titled "Surgical Tracking Methods And Fiber Optic Shape Sensing Devices Thereof." The '501 Application claims the benefit of U.S. Provisional Application Ser. No. 63/016,370, filed on Apr. 28, 2020. Both applications are incorporated herein by reference in their entirety.

TECHNICAL FIELD

The present disclosure relates generally to methods, systems, and apparatuses related to a computer-assisted surgical system that includes various hardware and software components that work together to enhance surgical workflows. The disclosed techniques may be applied to, for example, shoulder, hip, and knee arthroplasties, as well as other surgical interventions such as arthroscopic procedures, spinal procedures, maxillofacial procedures, rotator cuff procedures, ligament repair and replacement procedures.

BACKGROUND

During computer navigated orthopedic and sports medicine surgical procedures, various methods are used to track the positions of the patient's anatomy and of instruments relative to the patient's anatomy. Optical tracking systems (OTSs) are the most commonly used surgical tracking systems in commercial robotic platforms because of their relatively high accuracy and the relatively large workspace they can cover. However, current methods of tracking, including infrared tracking, electromagnetic (EM) tracking, and mechanical tracking, all have certain drawbacks that can make them challenging to use.

In particular, many OTSs require that a line-of-sight be maintained between the tracking device and the instrument to be tracked, which is not always possible in the operating theater and potentially precludes tracking of surgical instruments inside a patient's body. These computer-aided surgery (CAS) systems not only require line-of-sight, but are also only accurate within a defined volume. This volume is determined based on the camera's position and can be difficult to maintain throughout the surgical procedure, especially during manipulation of the patient's bony anatomy. OTSs also typically require additional skin incisions to be performed so that they can be rigidly attached to bone.

As another example, EM navigation systems also suffer from a number of disadvantages. Similar to line-of-sight tracking, it can be difficult to maintain an optimal clinical workflow while also satisfying the requirements of the EM system. The EM system only provides accurate measurements within a defined volume with respect to the position of the field generator. Further, metal, which may be commonly used during orthopedic and sports medicine surgical procedures, in the EM field can generate interference and degrade the accuracy of the measurements.

SUMMARY

Methods, non-transitory computer readable media, surgical tracking devices, and systems are illustrated that facilitate improved tracking in surgical environments. According to some embodiments, a method for anatomy location tracking is disclosed that includes attaching a fiber optical shape sensing (FOSS) device to one or more anatomical structures of a patient. The FOSS device includes an optical fiber comprising a plurality of cores each comprising at least one fiber Bragg grating (FBG) sensor. Reflectivity data is then generated based on detected reflection from the FBG sensors of broadband light introduced by a light source to the plurality of cores of the optical fiber of the FOSS device. One or more portions of the optical fiber of the FOSS device are registered within a coordinate system of at least one three dimensional model of the one or more anatomical structures of the patient. A location of at least the one or more portions of the optical fiber of the FOSS device are tracked based on the generated reflectivity data and the registration. One or more graphical displays output to a display device are then adjusted based on the tracked location. The one or more graphical displays include a representation of at least a portion of the at least one three dimensional model of the one or more anatomical structures of the patient.

According to some embodiments, each of the plurality of cores of the optical fiber of the FOSS device includes a plurality of FBG sensors. In these embodiments, the FOSS device is attached so as to be biased against the one or more anatomical structures of the patient. The generated reflectivity data in these embodiments represents a shape of at least a portion of the optical fiber of the FOSS device.

According to some embodiments, a hollow needle is driven into at least one of the one or more anatomical structures of the patient. The hollow needle includes an inner lumen in these embodiments. Additionally, at least one of the one or more portions of the optical fiber of the FOSS device is seated within the inner lumen of the hollow needle to attach the FOSS device to the at least one of the one or more anatomical structures of the patient.

According to some embodiments, the at least one of the one or more anatomical structures of the patient comprises soft tissue. In these embodiments, the hollow needle is positioned in the soft tissue.

According to some embodiments, a FOSS device is attached to at least one surgical instrument disposed in a surgical environment. The FOSS device includes an optical fiber including at least one core comprising at least one FBG sensor. Reflectivity data is generated based on detected reflection from the at least one FBG sensor of broadband light introduced by a light source to the at least one core of the optical fiber of the FOSS device. One or more portions of the optical fiber of the FOSS device are registered within a coordinate system of the surgical environment. A location of the one or more portions of the optical fiber of the FOSS device is tracked based on the generated reflectivity data and the registration. One or more graphical displays are output to a display device based on the tracked location. The one or more graphical displays include a representation associated with at least a portion of the at least one surgical instrument.

According to some embodiments, a location or an operation of the at least one surgical instrument is automatically controlled based on the tracked location of the one or more portions of the optical fiber of the FOSS device.

According to some embodiments, the at least one surgical instrument comprises a limb or joint of a robotic arm.

According to some embodiments, a determination is made when a collision of the limb or joint of the robotic arm, or an instrument held by the robotic arm, with another tracked object in the surgical environment is imminent based on the tracked location. The collision is prevented in these embodiments based on the automatic control of the location of the limb or joint of the robotic arm.

According to some embodiments, the at least one surgical instrument includes a flexible portion of a drill guide. In these embodiments, a guidewire for a femoral tunnel is placed based on the tracked location in order to define one or more of a trajectory or an orientation of the guidewire.

According to some embodiments, the at least one surgical instrument comprises two or more surgical instruments attached to the FOSS device.

According to some embodiments, a shaver or an ablator is automatically controlled based on the tracked location to remove one or more portions of an anatomical structure of a patient. In these embodiments, the one or more portions of the anatomical structure of the patient are defined preoperatively via one or more models.

According to some embodiments, the FOSS device is attached to the one or more anatomical structures of a patient. Another one or more portions of the optical fiber of the FOSS device are registered within one or more of the coordinate system of the surgical environment or at least one three dimensional model of the one or more anatomical structures of the patient. Additionally, another location of the another one or more portions of the optical fiber of the FOSS device is tracked based on the generated reflectivity data and the registration.

According to some embodiments, a method includes communicating via one or more communication networks with a surgical computer configured to implement a navigated surgical procedure in order to automatically control the location or the operation of the at least one surgical instrument.

According to some embodiments, a method for surgical instrument flexibility tracking is disclosed. In these embodiments, a FOSS device is attached to at least one surgical instrument disposed in a surgical environment. The FOSS device includes an optical fiber comprising a plurality of cores each comprising at least one FBG sensor. Reflectivity data generated based on detected reflection from the at least one FBG sensor of broadband light introduced by a light source to the plurality of cores of the optical fiber of the FOSS device. A flexion of the one or more portions of the optical fiber of the FOSS device is then determined based on the generated reflectivity data. A location or an operation of the at least one surgical instrument is automatically controlled based on the determined flexion of the one or more portions of the optical fiber of the FOSS device.

According to some embodiments, one or more portions of the optical fiber of the FOSS device are then registered within a coordinate system of the surgical environment.

According to some embodiments, each of the plurality of cores comprises a plurality of FBG sensors configured to facilitate tracking of a shape of the one or more portions of the optical fiber of the FOSS device.

According to some embodiments the location or the operation of the at least one surgical instrument is automatically controlled when the determined flexion exceeds a flexion threshold.

According to some embodiments, a method includes communicating via one or more communication networks with a surgical computer configured to implement a navigated surgical procedure in order to automatically control the location or the operation of the at least one surgical instrument.

According to some embodiments, the at least one surgical instrument includes a shaver comprising a burr tip configured to remove one or more anatomical structures of a patient.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 3A depicts an alternative example of an electromagnetic sensor device, with three perpendicular coils, according to some embodiments.

FIG. 3B depicts an alternative example of an electromagnetic sensor device, with two nonparallel, affixed coils, according to some embodiments.

FIG. 3C depicts an alternative example of an electromagnetic sensor device, with two nonparallel, separate coils, according to some embodiments.

FIG. 8 depicts exemplary fiber optic shape sensing (FOSS) device configurations that can be used to facilitate improved tracking of patient anatomy and/or instruments in surgical environments in accordance with an embodiment.

FIGS. 9A-B depict an exemplary FOSS device that facilitates shape sensing in three dimensions using three single mode cores with strain sensors in accordance with an embodiment.

DETAILED DESCRIPTION

This disclosure is not limited to the particular systems, devices and methods described, as these may vary. The terminology used in the description is for the purpose of describing the particular versions or embodiments only and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Definitions

For the purposes of this disclosure, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

For the purposes of this disclosure, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

Although much of this disclosure refers to surgeons or other medical professionals by specific job title or role, nothing in this disclosure is intended to be limited to a specific job title or function. Surgeons or medical professionals can include any doctor, nurse, medical professional, or technician. Any of these terms or job titles can be used interchangeably with the user of the systems disclosed herein unless otherwise explicitly demarcated. For example, a reference to a surgeon also could apply, in some embodiments to a technician or nurse.

Figure 1:
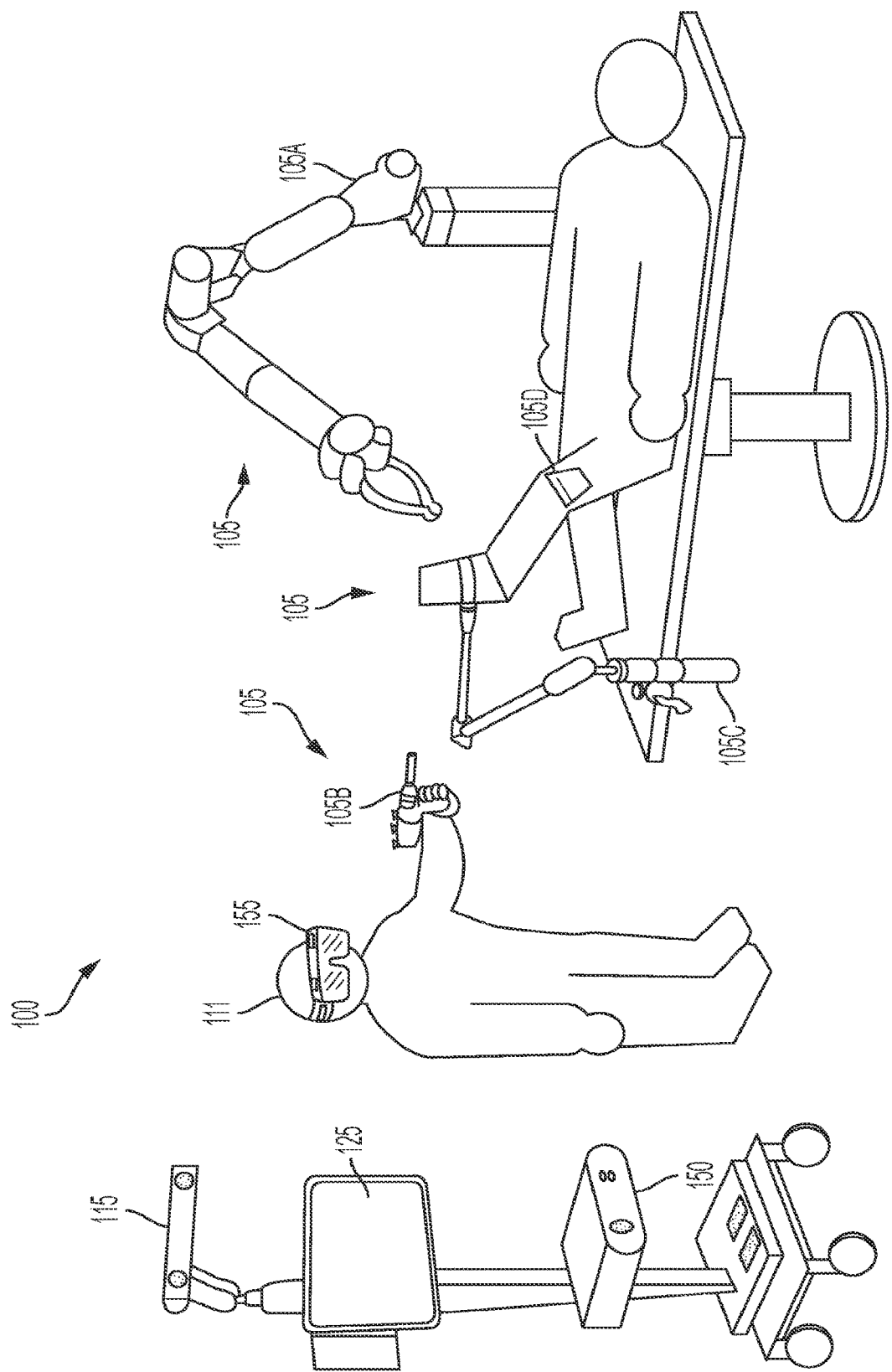
FIG. 1 depicts an operating theatre including an illustrative computer-assisted surgical system (CASS) in accordance with an embodiment.

The systems, methods, and devices disclosed herein are particularly well adapted for surgical procedures that utilize surgical navigation systems, such as the NAVIO® surgical navigation system. NAVIO is a registered trademark of BLUE BELT TECHNOLOGIES, INC. of Pittsburgh, PA, which is a subsidiary of SMITH & NEPHEW, INC. of Memphis, TN. CASS Ecosystem Overview FIG. 1 provides an illustration of an example computer-assisted surgical system (CASS) 100, according to some embodiments. As described in further detail in the sections that follow, the CASS uses computers, robotics, and imaging technology to aid surgeons in performing orthopedic surgery procedures such as total knee arthroplasty (TKA) or total hip arthroplasty (THA). For example, surgical navigation systems can aid surgeons in locating patient anatomical structures, guiding surgical instruments, and implanting medical devices with a high degree of accuracy. Surgical navigation systems such as the CASS 100 often employ various forms of computing technology to perform a wide variety of standard and minimally invasive surgical procedures and techniques. Moreover, these systems allow surgeons to more accurately plan, track and navigate the placement of instruments and implants relative to the body of a patient, as well as conduct pre-operative and intra-operative body imaging.

An Effector Platform 105 positions surgical tools relative to a patient during surgery. The exact components of the Effector Platform 105 will vary, depending on the embodiment employed. For example, for a knee surgery, the Effector Platform 105 may include an End Effector 105B that holds surgical tools or instruments during their use. The End Effector 105B may be a handheld device or instrument used by the surgeon (e.g., a NAVIO® hand piece or a cutting guide or jig) or, alternatively, the End Effector 105B can include a device or instrument held or positioned by a Robotic Arm 105A. While one Robotic Arm 105A is illustrated in FIG. 1, in some embodiments there may be multiple devices. As examples, there may be one Robotic Arm 105A on each side of an operating table T or two devices on one side of the table T. The Robotic Arm 105A may be mounted directly to the table T, be located next to the table T on a floor platform (not shown), mounted on a floor-to-ceiling pole, or mounted on a wall or ceiling of an operating room. The floor platform may be fixed or moveable. In one particular embodiment, the robotic arm 105A is mounted on a floor-to-ceiling pole located between the patient's legs or feet. In some embodiments, the End Effector 105B may include a suture holder or a stapler to assist in closing wounds. Further, in the case of two robotic arms 105A, the surgical computer 150 can drive the robotic arms 105A to work together to suture the wound at closure. Alternatively, the surgical computer 150 can drive one or more robotic arms 105A to staple the wound at closure.

The Effector Platform 105 can include a Limb Positioner 105C for positioning the patient's limbs during surgery. One example of a Limb Positioner 105C is the SMITH AND NEPHEW SPIDER2 system. The Limb Positioner 105C may be operated manually by the surgeon or alternatively change limb positions based on instructions received from the Surgical Computer 150 (described below). While one Limb Positioner 105C is illustrated in FIG. 1, in some embodiments there may be multiple devices. As examples, there may be one Limb Positioner 105C on each side of the operating table T or two devices on one side of the table T. The Limb Positioner 105C may be mounted directly to the table T, be located next to the table T on a floor platform (not shown), mounted on a pole, or mounted on a wall or ceiling of an operating room. In some embodiments, the Limb Positioner 105C can be used in non-conventional ways, such as a retractor or specific bone holder. The Limb Positioner 105C may include, as examples, an ankle boot, a soft tissue clamp, a bone clamp, or a soft-tissue retractor spoon, such as a hooked, curved, or angled blade. In some embodiments, the Limb Positioner 105C may include a suture holder to assist in closing wounds.

The Effector Platform 105 may include tools, such as a screwdriver, light or laser, to indicate an axis or plane, bubble level, pin driver, pin puller, plane checker, pointer, finger, or some combination thereof.

Resection Equipment 110 (not shown in FIG. 1) performs bone or tissue resection using, for example, mechanical, ultrasonic, or laser techniques. Examples of Resection Equipment 110 include drilling devices, burring devices, oscillatory sawing devices, vibratory impaction devices, reamers, ultrasonic bone cutting devices, radio frequency ablation devices, reciprocating devices (such as a rasp or broach), and laser ablation systems. In some embodiments, the Resection Equipment 110 is held and operated by the surgeon during surgery. In other embodiments, the Effector Platform 105 may be used to hold the Resection Equipment 110 during use.

The Effector Platform 105 also can include a cutting guide or jig 105D that is used to guide saws or drills used to resect tissue during surgery. Such cutting guides 105D can be formed integrally as part of the Effector Platform 105 or Robotic Arm 105A, or cutting guides can be separate structures that can be matingly and/or removably attached to the Effector Platform 105 or Robotic Arm 105A. The Effector Platform 105 or Robotic Arm 105A can be controlled by the CASS 100 to position a cutting guide or jig 105D adjacent to the patient's anatomy in accordance with a pre-operatively or intraoperatively developed surgical plan such that the cutting guide or jig will produce a precise bone cut in accordance with the surgical plan.

The Tracking System 115 uses one or more sensors to collect real-time position data that locates the patient's anatomy and surgical instruments. For example, for TKA procedures, the Tracking System may provide a location and orientation of the End Effector 105B during the procedure. In addition to positional data, data from the Tracking System 115 also can be used to infer velocity/acceleration of anatomy/instrumentation, which can be used for tool control. In some embodiments, the Tracking System 115 may use a tracker array attached to the End Effector 105B to determine the location and orientation of the End Effector 105B. The position of the End Effector 105B may be inferred based on the position and orientation of the Tracking System 115 and a known relationship in three-dimensional space between the Tracking System 115 and the End Effector 105B. Various types of tracking systems may be used in various embodiments of the present invention including, without limitation, Infrared (IR) tracking systems, electromagnetic (EM) tracking systems, video or image based tracking systems, and ultrasound registration and tracking systems. Using the data provided by the tracking system 115, the surgical computer 150 can detect objects and prevent collision. For example, the surgical computer 150 can prevent the Robotic Arm 105A and/or the End Effector 105B from colliding with soft tissue.

Any suitable tracking system can be used for tracking surgical objects and patient anatomy in the surgical theatre. For example, a combination of IR and visible light cameras can be used in an array. Various illumination sources, such as an IR LED light source, can illuminate the scene allowing three-dimensional imaging to occur. In some embodiments, this can include stereoscopic, tri-scopic, quad-scopic, etc. imaging. In addition to the camera array, which in some embodiments is affixed to a cart, additional cameras can be placed throughout the surgical theatre. For example, handheld tools or headsets worn by operators/surgeons can include imaging capability that communicates images back to a central processor to correlate those images with images captured by the camera array. This can give a more robust image of the environment for modeling using multiple perspectives. Furthermore, some imaging devices may be of suitable resolution or have a suitable perspective on the scene to pick up information stored in quick response (QR) codes or barcodes. This can be helpful in identifying specific objects not manually registered with the system. In some embodiments, the camera may be mounted on the Robotic Arm 105A.

Although, as discussed herein, the majority of tracking and/or navigation techniques utilize image-based tracking systems (e.g., IR tracking systems, video or image based tracking systems, etc.). However, electromagnetic (EM) based tracking systems are becoming more common for a variety of reasons. For example, implantation of standard optical trackers requires tissue resection (e.g., down to the cortex) as well as subsequent drilling and driving of cortical pins. Additionally, because optical trackers require a direct line of sight with a tracking system, the placement of such trackers may need to be far from the surgical site to ensure they do not restrict the movement of a surgeon or medical professional.

Figure 2:
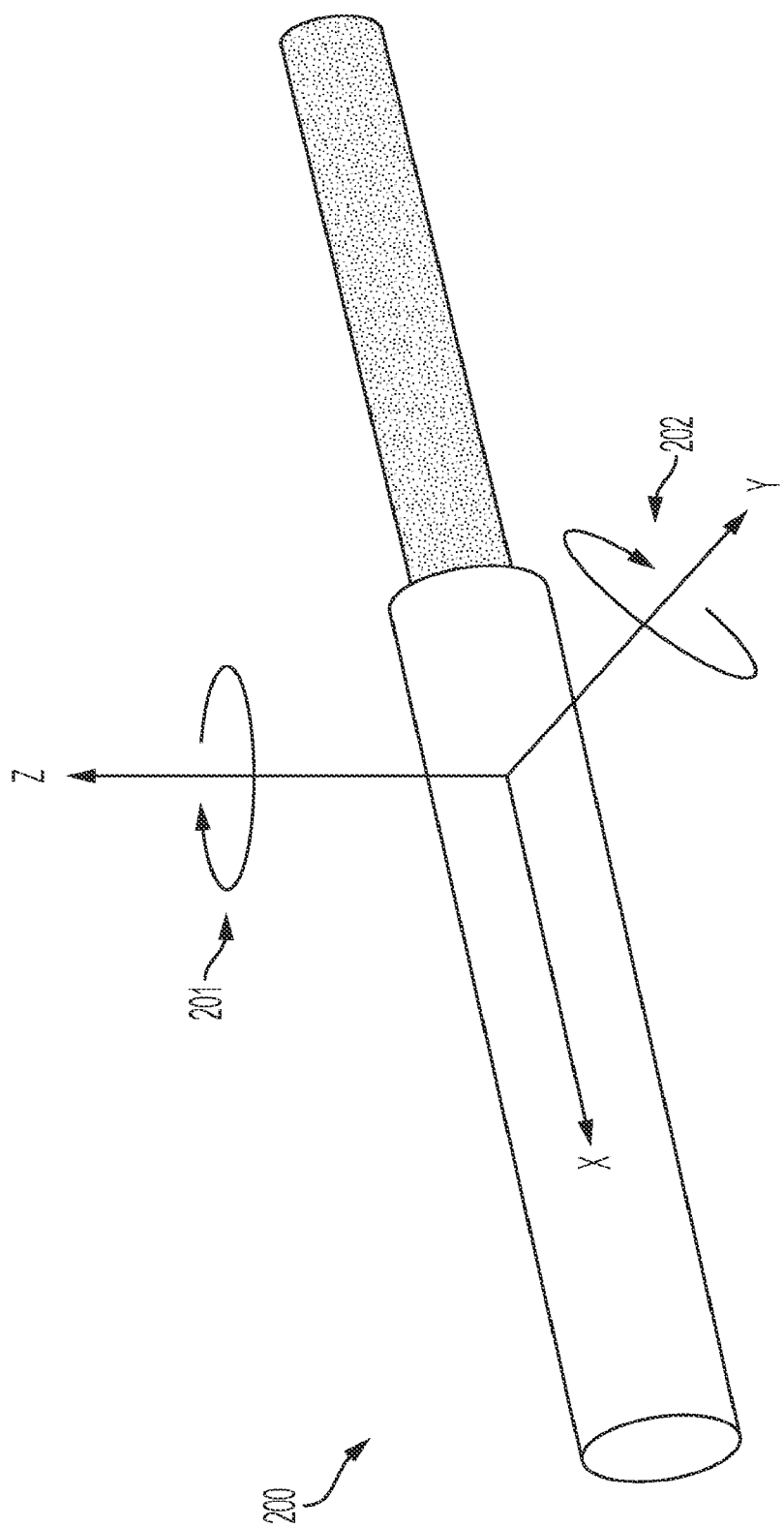
FIG. 2 depicts an example of an electromagnetic sensor device according to some embodiments.

Generally, EM based tracking devices include one or more wire coils and a reference field generator. The one or more wire coils may be energized (e.g., via a wired or wireless power supply). Once energized, the coil creates an electromagnetic field that can be detected and measured (e.g., by the reference field generator or an additional device) in a manner that allows for the location and orientation of the one or more wire coils to be determined. As should be understood by someone of ordinary skill in the art, a single coil, such as is shown in FIG. 2, is limited to detecting five (5) total degrees-of-freedom (DOF). For example, sensor 200 may be able to track/determine movement in the X, Y, or Z direction, as well as rotation around the Y-axis 202 or Z-axis 201. However, because of the electromagnetic properties of a coil, it is not possible to properly track rotational movement around the X axis.

Accordingly, in most electromagnetic tracking applications, a three coil system, such as that shown in FIG. 3A is used to enable tracking in all six degrees of freedom that are possible for a rigid body moving in a three-dimensional space (i.e.., forward/backward 310, up/down 320, left/right 330, roll 340, pitch 350, and yaw 360). However, the inclusion of two additional coils and the 90° offset angles at which they are positioned may require the tracking device to be much larger. Alternatively, as one of skill in the art would know, less than three full coils may be used to track all 6DOF. In some EM based tracking devices, two coils may be affixed to each other, such as is shown in FIG. 3B. Because the two coils 301B and 302B are rigidly affixed to each other, not perfectly parallel, and have locations that are known relative to each other, it is possible to determine the sixth degree of freedom 303B with this arrangement.

Although the use of two affixed coils (e.g., 301B and 302B) allows for EM based tracking in 6DOF, the sensor device is substantially larger in diameter than a single coil because of the additional coil. Thus, the practical application of using an EM based tracking system in a surgical environment may require tissue resection and drilling of a portion of the patient bone to allow for insertion of a EM tracker. Alternatively, in some embodiments, it may be possible to implant/insert a single coil, or 5DOF EM tracking device, into a patient bone using only a pin (e.g., without the need to drill or carve out substantial bone).

Thus, as described herein, a solution is needed for which the use of an EM tracking system can be restricted to devices small enough to be inserted/embedded using a small diameter needle or pin (i.e.., without the need to create a new incision or large diameter opening in the bone). Accordingly, in some embodiments, a second 5DOF sensor, which is not attached to the first, and thus has a small diameter, may be used to track all 6DOF. Referring now to FIG. 3C, in some embodiments, two 5DOF EM sensors (e.g., 301C and 302C) may be inserted into the patient (e.g., in a patient bone) at different locations and with different angular orientations (e.g., angle 303C is non-zero).

Figure 4:
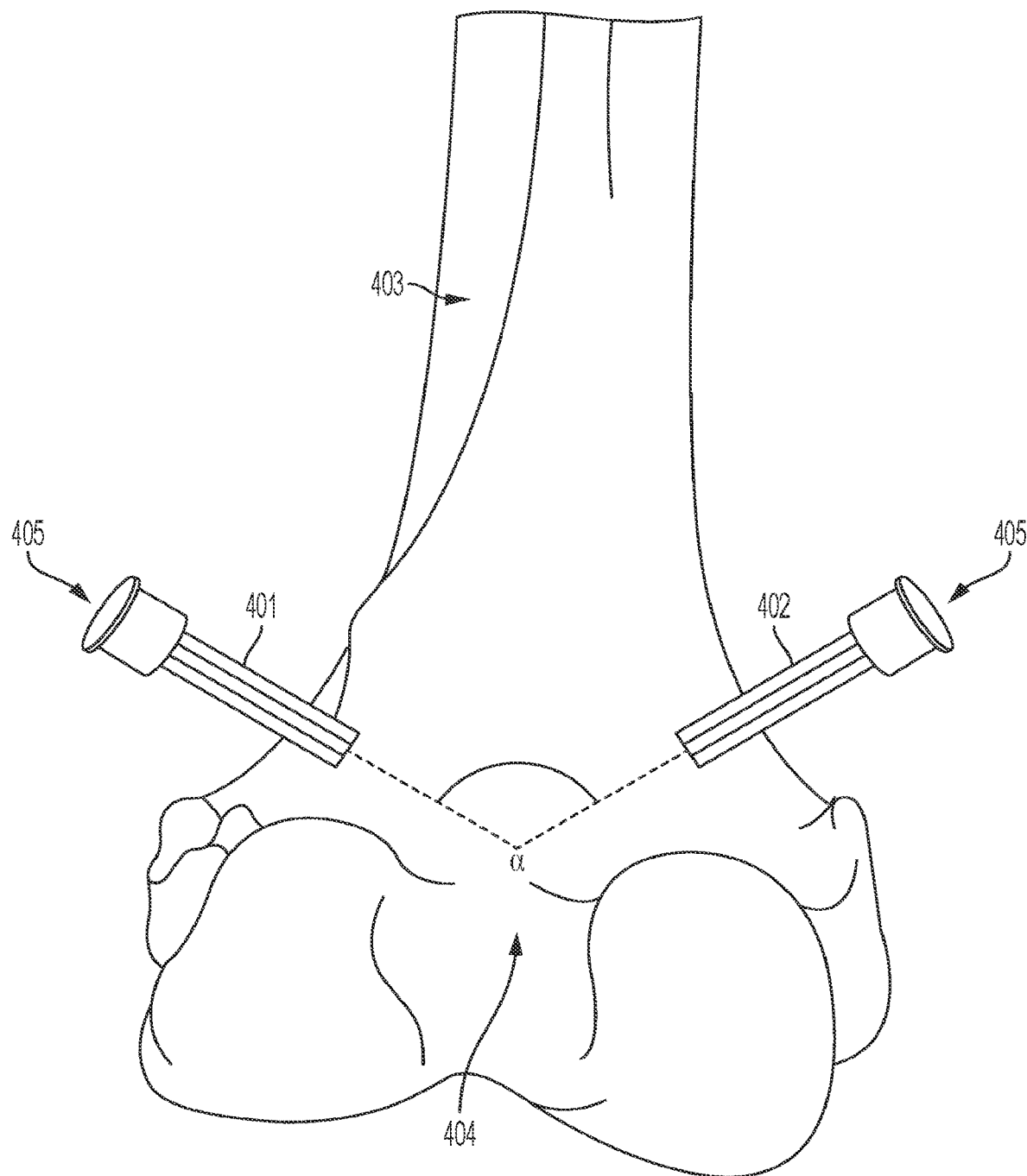
FIG. 4 depicts an example of electromagnetic sensor devices and a patient bone according to some embodiments.

Referring now to FIG. 4, an example embodiment is shown in which a first 5DOF EM sensor 401 and a second 5DOF EM sensor 402 are inserted into the patient bone 403 using a standard hollow needle 405 that is typical in most OR(s). In a further embodiment, the first sensor 401 and the second sensor 402 may have an angle offset of "α" 404. In some embodiments, it may be necessary for the offset angle "α" 404 to be greater than a predetermined value (e.g., a minimum angle of 0.50°, 0.75°, etc.). This minimum value may, in some embodiments, be determined by the CASS and provided to the surgeon or medical professional during the surgical plan. In some embodiments, a minimum value may be based on one or more factors, such as, for example, the orientation accuracy of the tracking system, a distance between the first and second EM sensors. The location of the field generator, a location of the field detector, a type of EM sensor, a quality of the EM sensor, patient anatomy, and the like.

Accordingly, as discussed herein, in some embodiments, a pin/needle (e.g., a cannulated mounting needle, etc.) may be used to insert one or more EM sensors. Generally, the pin/needle would be a disposable component, while the sensors themselves may be reusable. However, it should be understood that this is only one potential system, and that various other systems may be used in which the pin/needle and/or EM sensors are independently disposable or reusable. In a further embodiment, the EM sensors may be affixed to the mounting needle/pin (e.g., using a luer-lock fitting or the like), which can allow for quick assembly and disassembly. In additional embodiments, the EM sensors may utilize an alternative sleeve and/or anchor system that allows for minimally invasive placement of the sensors.

In another embodiment, the above systems may allow for a multi-sensor navigation system that can detect and correct for field distortions that plague electromagnetic tracking systems. It should be understood that field distortions may result from movement of any ferromagnetic materials within the reference field. Thus, as one of ordinary skill in the art would know, a typical OR has a large number of devices (e.g., an operating table, LCD displays, lighting equipment, imaging systems, surgical instruments, etc.) that may cause interference. Furthermore, field distortions are notoriously difficult to detect. The use of multiple EM sensors enables the system to detect field distortions accurately, and/or to warn a user that the current position measurements may not be accurate. Because the sensors are rigidly fixed to the bony anatomy (e.g., via the pin/needle), relative measurement of sensor positions (X, Y, Z) may be used to detect field distortions. By way of non-limiting example, in some embodiments, after the EM sensors are fixed to the bone, the relative distance between the two sensors is known and should remain constant. Thus, any change in this distance could indicate the presence of a field distortion.

In some embodiments, specific objects can be manually registered by a surgeon with the system preoperatively or intraoperatively. For example, by interacting with a user interface, a surgeon may identify the starting location for a tool or a bone structure. By tracking fiducial marks associated with that tool or bone structure, or by using other conventional image tracking modalities, a processor may track that tool or bone as it moves through the environment in a three-dimensional model.

In some embodiments, certain markers, such as fiducial marks that identify individuals, important tools, or bones in the theater may include passive or active identifiers that can be picked up by a camera or camera array associated with the tracking system. For example, an IR LED can flash a pattern that conveys a unique identifier to the source of that pattern, providing a dynamic identification mark. Similarly, one or two dimensional optical codes (barcode, QR code, etc.) can be affixed to objects in the theater to provide passive identification that can occur based on image analysis. If these codes are placed asymmetrically on an object, they also can be used to determine an orientation of an object by comparing the location of the identifier with the extents of an object in an image. For example, a QR code may be placed in a corner of a tool tray, allowing the orientation and identity of that tray to be tracked. Other tracking modalities are explained throughout. For example, in some embodiments, augmented reality headsets can be worn by surgeons and other staff to provide additional camera angles and tracking capabilities.

In addition to optical tracking, certain features of objects can be tracked by registering physical properties of the object and associating them with objects that can be tracked, such as fiducial marks fixed to a tool or bone. For example, a surgeon may perform a manual registration process whereby a tracked tool and a tracked bone can be manipulated relative to one another. By impinging the tip of the tool against the surface of the bone, a three-dimensional surface can be mapped for that bone that is associated with a position and orientation relative to the frame of reference of that fiducial mark. By optically tracking the position and orientation (pose) of the fiducial mark associated with that bone, a model of that surface can be tracked with an environment through extrapolation.

The registration process that registers the CASS 100 to the relevant anatomy of the patient also can involve the use of anatomical landmarks, such as landmarks on a bone or cartilage. For example, the CASS 100 can include a 3D model of the relevant bone or joint and the surgeon can intraoperatively collect data regarding the location of bony landmarks on the patient's actual bone using a probe that is connected to the CASS. Bony landmarks can include, for example, the medial malleolus and lateral malleolus, the ends of the proximal femur and distal tibia, and the center of the hip joint. The CASS 100 can compare and register the location data of bony landmarks collected by the surgeon with the probe with the location data of the same landmarks in the 3D model. Alternatively, the CASS 100 can construct a 3D model of the bone or joint without pre-operative image data by using location data of bony landmarks and the bone surface that are collected by the surgeon using a CASS probe or other means. The registration process also can include determining various axes of a joint. For example, for a TKA the surgeon can use the CASS 100 to determine the anatomical and mechanical axes of the femur and tibia. The surgeon and the CASS 100 can identify the center of the hip joint by moving the patient's leg in a spiral direction (i.e., circumduction) so the CASS can determine where the center of the hip joint is located.

A Tissue Navigation System 120 (not shown in FIG. 1) provides the surgeon with intraoperative, real-time visualization for the patient's bone, cartilage, muscle, nervous, and/or vascular tissues surrounding the surgical area. Examples of systems that may be employed for tissue navigation include fluorescent imaging systems and ultrasound systems.

The Display 125 provides graphical user interfaces (GUIs) that display images collected by the Tissue Navigation System 120 as well other information relevant to the surgery. For example, in one embodiment, the Display 125 overlays image information collected from various modalities (e.g., CT, MRI, X-ray, fluorescent, ultrasound, etc.) collected pre-operatively or intra-operatively to give the surgeon various views of the patient's anatomy as well as real-time conditions. The Display 125 may include, for example, one or more computer monitors. As an alternative or supplement to the Display 125, one or more members of the surgical staff may wear an Augmented Reality (AR) Head Mounted Device (HMD). For example, in FIG. 1 the Surgeon 111 is wearing an AR HMD 155 that may, for example, overlay pre-operative image data on the patient or provide surgical planning suggestions. Various example uses of the AR HMD 155 in surgical procedures are detailed in the sections that follow.

Surgical Computer 150 provides control instructions to various components of the CASS 100, collects data from those components, and provides general processing for various data needed during surgery. In some embodiments, the Surgical Computer 150 is a general purpose computer. In other embodiments, the Surgical Computer 150 may be a parallel computing platform that uses multiple central processing units (CPUs) or graphics processing units (GPU) to perform processing. In some embodiments, the Surgical Computer 150 is connected to a remote server over one or more computer networks (e.g., the Internet). The remote server can be used, for example, for storage of data or execution of computationally intensive processing tasks.

Various techniques generally known in the art can be used for connecting the Surgical Computer 150 to the other components of the CASS 100. Moreover, the computers can connect to the Surgical Computer 150 using a mix of technologies. For example, the End Effector 105B may connect to the Surgical Computer 150 over a wired (i.e.., serial) connection. The Tracking System 115, Tissue Navigation System 120, and Display 125 can similarly be connected to the Surgical Computer 150 using wired connections. Alternatively, the Tracking System 115, Tissue Navigation System 120, and Display 125 may connect to the Surgical Computer 150 using wireless technologies such as, without limitation, Wi-Fi, Bluetooth, Near Field Communication (NFC), or ZigBee.

Powered Impaction and Acetabular Reamer Devices

Part of the flexibility of the CASS design described above with respect to FIG. 1 is that additional or alternative devices can be added to the CASS 100 as necessary to support particular surgical procedures. For example, in the context of hip surgeries, the CASS 100 may include a powered impaction device. Impaction devices are designed to repeatedly apply an impaction force that the surgeon can use to perform activities such as implant alignment. For example, within a total hip arthroplasty (THA), a surgeon will often insert a prosthetic acetabular cup into the implant host's acetabulum using an impaction device. Although impaction devices can be manual in nature (e.g., operated by the surgeon striking an impactor with a mallet), powered impaction devices are generally easier and quicker to use in the surgical setting. Powered impaction devices may be powered, for example, using a battery attached to the device. Various attachment pieces may be connected to the powered impaction device to allow the impaction force to be directed in various ways as needed during surgery. Also, in the context of hip surgeries, the CASS 100 may include a powered, robotically controlled end effector to ream the acetabulum to accommodate an acetabular cup implant.

In a robotically-assisted THA, the patient's anatomy can be registered to the CASS 100 using CT or other image data, the identification of anatomical landmarks, tracker arrays attached to the patient's bones, and one or more cameras. Tracker arrays can be mounted on the iliac crest using clamps and/or bone pins and such trackers can be mounted externally through the skin or internally (either posterolaterally or anterolaterally) through the incision made to perform the THA. For a THA, the CASS 100 can utilize one or more femoral cortical screws inserted into the proximal femur as checkpoints to aid in the registration process. The CASS 100 also can utilize one or more checkpoint screws inserted into the pelvis as additional checkpoints to aid in the registration process. Femoral tracker arrays can be secured to or mounted in the femoral cortical screws. The CASS 100 can employ steps where the registration is verified using a probe that the surgeon precisely places on key areas of the proximal femur and pelvis identified for the surgeon on the display 125. Trackers can be located on the robotic arm 105A or end effector 105B to register the arm and/or end effector to the CASS 100. The verification step also can utilize proximal and distal femoral checkpoints. The CASS 100 can utilize color prompts or other prompts to inform the surgeon that the registration process for the relevant bones and the robotic arm 105A or end effector 105B has been verified to a certain degree of accuracy (e.g., within 1 mm).

For a THA, the CASS 100 can include a broach tracking option using femoral arrays to allow the surgeon to intraoperatively capture the broach position and orientation and calculate hip length and offset values for the patient. Based on information provided about the patient's hip joint and the planned implant position and orientation after broach tracking is completed, the surgeon can make modifications or adjustments to the surgical plan.

For a robotically-assisted THA, the CASS 100 can include one or more powered reamers connected or attached to a robotic arm 105A or end effector 105B that prepares the pelvic bone to receive an acetabular implant according to a surgical plan. The robotic arm 105A and/or end effector 105B can inform the surgeon and/or control the power of the reamer to ensure that the acetabulum is being resected (reamed) in accordance with the surgical plan. For example, if the surgeon attempts to resect bone outside of the boundary of the bone to be resected in accordance with the surgical plan, the CASS 100 can power off the reamer or instruct the surgeon to power off the reamer. The CASS 100 can provide the surgeon with an option to turn off or disengage the robotic control of the reamer. The display 125 can depict the progress of the bone being resected (reamed) as compared to the surgical plan using different colors. The surgeon can view the display of the bone being resected (reamed) to guide the reamer to complete the reaming in accordance with the surgical plan. The CASS 100 can provide visual or audible prompts to the surgeon to warn the surgeon that resections are being made that are not in accordance with the surgical plan.

Following reaming, the CASS 100 can employ a manual or powered impactor that is attached or connected to the robotic arm 105A or end effector 105B to impact trial implants and final implants into the acetabulum. The robotic arm 105A and/or end effector 105B can be used to guide the impactor to impact the trial and final implants into the acetabulum in accordance with the surgical plan. The CASS 100 can cause the position and orientation of the trial and final implants vis-à-vis the bone to be displayed to inform the surgeon as to how the trial and final implant's orientation and position compare to the surgical plan, and the display 125 can show the implant's position and orientation as the surgeon manipulates the leg and hip. The CASS 100 can provide the surgeon with the option of re-planning and re-doing the reaming and implant impaction by preparing a new surgical plan if the surgeon is not satisfied with the original implant position and orientation.

Preoperatively, the CASS 100 can develop a proposed surgical plan based on a three dimensional model of the hip joint and other information specific to the patient, such as the mechanical and anatomical axes of the leg bones, the epicondylar axis, the femoral neck axis, the dimensions (e.g., length) of the femur and hip, the midline axis of the hip joint, the ASIS axis of the hip joint, and the location of anatomical landmarks such as the lesser trochanter landmarks, the distal landmark, and the center of rotation of the hip joint. The CASS-developed surgical plan can provide a recommended optimal implant size and implant position and orientation based on the three dimensional model of the hip joint and other information specific to the patient. The CASS-developed surgical plan can include proposed details on offset values, inclination and anteversion values, center of rotation, cup size, medialization values, superior-inferior fit values, femoral stem sizing and length.

For a THA, the CASS-developed surgical plan can be viewed preoperatively and intraoperatively, and the surgeon can modify CASS-developed surgical plan preoperatively or intraoperatively. The CASS-developed surgical plan can display the planned resection to the hip joint and superimpose the planned implants onto the hip joint based on the planned resections. The CASS 100 can provide the surgeon with options for different surgical workflows that will be displayed to the surgeon based on a surgeon's preference. For example, the surgeon can choose from different workflows based on the number and types of anatomical landmarks that are checked and captured and/or the location and number of tracker arrays used in the registration process.

According to some embodiments, a powered impaction device used with the CASS 100 may operate with a variety of different settings. In some embodiments, the surgeon adjusts settings through a manual switch or other physical mechanism on the powered impaction device. In other embodiments, a digital interface may be used that allows setting entry, for example, via a touchscreen on the powered impaction device. Such a digital interface may allow the available settings to vary based, for example, on the type of attachment piece connected to the power attachment device. In some embodiments, rather than adjusting the settings on the powered impaction device itself, the settings can be changed through communication with a robot or other computer system within the CASS 100. Such connections may be established using, for example, a Bluetooth or Wi-Fi networking module on the powered impaction device. In another embodiment, the impaction device and end pieces may contain features that allow the impaction device to be aware of what end piece (cup impactor, broach handle, etc.) is attached with no action required by the surgeon, and adjust the settings accordingly. This may be achieved, for example, through a QR code, barcode, RFID tag, or other method.

Examples of the settings that may be used include cup impaction settings (e.g., single direction, specified frequency range, specified force and/or energy range); broach impaction settings (e.g., dual direction/oscillating at a specified frequency range, specified force and/or energy range); femoral head impaction settings (e.g., single direction/single blow at a specified force or energy); and stem impaction settings (e.g., single direction at specified frequency with a specified force or energy). Additionally, in some embodiments, the powered impaction device includes settings related to acetabular liner impaction (e.g., single direction/single blow at a specified force or energy). There may be a plurality of settings for each type of liner such as poly, ceramic, oxinium, or other materials. Furthermore, the powered impaction device may offer settings for different bone quality based on preoperative testing/imaging/knowledge and/or intraoperative assessment by surgeon. In some embodiments, the powered impactor device may have a dual function. For example, the powered impactor device not only could provide reciprocating motion to provide an impact force, but also could provide reciprocating motion for a broach or rasp.

In some embodiments, the powered impaction device includes feedback sensors that gather data during instrument use and send data to a computing device, such as a controller within the device or the Surgical Computer 150. This computing device can then record the data for later analysis and use. Examples of the data that may be collected include, without limitation, sound waves, the predetermined resonance frequency of each instrument, reaction force or rebound energy from patient bone, location of the device with respect to imaging (e.g., fluoro, CT, ultrasound, MRI, etc.) registered bony anatomy, and/or external strain gauges on bones.

Once the data is collected, the computing device may execute one or more algorithms in real-time or near real-time to aid the surgeon in performing the surgical procedure. For example, in some embodiments, the computing device uses the collected data to derive information such as the proper final broach size (femur); when the stem is fully seated (femur side); or when the cup is seated (depth and/or orientation) for a THA. Once the information is known, it may be displayed for the surgeon's review, or it may be used to activate haptics or other feedback mechanisms to guide the surgical procedure.

Additionally, the data derived from the aforementioned algorithms may be used to drive operation of the device. For example, during insertion of a prosthetic acetabular cup with a powered impaction device, the device may automatically extend an impaction head (e.g., an end effector) moving the implant into the proper location, or turn the power off to the device once the implant is fully seated. In one embodiment, the derived information may be used to automatically adjust settings for quality of bone where the powered impaction device should use less power to mitigate femoral/acetabular/pelvic fracture or damage to surrounding tissues.

Robotic Arm

In some embodiments, the CASS 100 includes a robotic arm 105A that serves as an interface to stabilize and hold a variety of instruments used during the surgical procedure. For example, in the context of a hip surgery, these instruments may include, without limitation, retractors, a sagittal or reciprocating saw, the reamer handle, the cup impactor, the broach handle, and the stem inserter. The robotic arm 105A may have multiple degrees of freedom (like a Spider device), and have the ability to be locked in place (e.g., by a press of a button, voice activation, a surgeon removing a hand from the robotic arm, or other method).

In some embodiments, movement of the robotic arm 105A may be effectuated by use of a control panel built into the robotic arm system. For example, a display screen may include one or more input sources, such as physical buttons or a user interface having one or more icons, that direct movement of the robotic arm 105A. The surgeon or other healthcare professional may engage with the one or more input sources to position the robotic arm 105A when performing a surgical procedure.

A tool or an end effector 105B attached or integrated into a robotic arm 105A may include, without limitation, a burring device, a scalpel, a cutting device, a retractor, a joint tensioning device, or the like. In embodiments in which an end effector 105B is used, the end effector may be positioned at the end of the robotic arm 105A such that any motor control operations are performed within the robotic arm system. In embodiments in which a tool is used, the tool may be secured at a distal end of the robotic arm 105A, but motor control operation may reside within the tool itself.

The robotic arm 105A may be motorized internally to both stabilize the robotic arm, thereby preventing it from falling and hitting the patient, surgical table, surgical staff, etc., and to allow the surgeon to move the robotic arm without having to fully support its weight. While the surgeon is moving the robotic arm 105A, the robotic arm may provide some resistance to prevent the robotic arm from moving too fast or having too many degrees of freedom active at once. The position and the lock status of the robotic arm 105A may be tracked, for example, by a controller or the Surgical Computer 150.

In some embodiments, the robotic arm 105A can be moved by hand (e.g., by the surgeon) or with internal motors into its ideal position and orientation for the task being performed. In some embodiments, the robotic arm 105A may be enabled to operate in a "free" mode that allows the surgeon to position the arm into a desired position without being restricted. While in the free mode, the position and orientation of the robotic arm 105A may still be tracked as described above. In one embodiment, certain degrees of freedom can be selectively released upon input from user (e.g., surgeon) during specified portions of the surgical plan tracked by the Surgical Computer 150. Designs in which a robotic arm 105A is internally powered through hydraulics or motors or provides resistance to external manual motion through similar means can be described as powered robotic arms, while arms that are manually manipulated without power feedback, but which may be manually or automatically locked in place, may be described as passive robotic arms.

A robotic arm 105A or end effector 105B can include a trigger or other means to control the power of a saw or drill. Engagement of the trigger or other means by the surgeon can cause the robotic arm 105A or end effector 105B to transition from a motorized alignment mode to a mode where the saw or drill is engaged and powered on. Additionally, the CASS 100 can include a foot pedal (not shown) that causes the system to perform certain functions when activated. For example, the surgeon can activate the foot pedal to instruct the CASS 100 to place the robotic arm 105A or end effector 105B in an automatic mode that brings the robotic arm or end effector into the proper position with respect to the patient's anatomy in order to perform the necessary resections. The CASS 100 also can place the robotic arm 105A or end effector 105B in a collaborative mode that allows the surgeon to manually manipulate and position the robotic arm or end effector into a particular location. The collaborative mode can be configured to allow the surgeon to move the robotic arm 105A or end effector 105B medially or laterally, while restricting movement in other directions. As discussed, the robotic arm 105A or end effector 105B can include a cutting device (saw, drill, and burr) or a cutting guide or jig 105D that will guide a cutting device. In other embodiments, movement of the robotic arm 105A or robotically controlled end effector 105B can be controlled entirely by the CASS 100 without any, or with only minimal, assistance or input from a surgeon or other medical professional. In still other embodiments, the movement of the robotic arm 105A or robotically controlled end effector 105B can be controlled remotely by a surgeon or other medical professional using a control mechanism separate from the robotic arm or robotically controlled end effector device, for example using a joystick or interactive monitor or display control device.

The examples below describe uses of the robotic device in the context of a hip surgery; however, it should be understood that the robotic arm may have other applications for surgical procedures involving knees, shoulders, etc. One example of use of a robotic arm in the context of forming an anterior cruciate ligament (ACL) graft tunnel is described in WIPO Publication No. WO 2020/047051, filed Aug. 28, 2019, entitled "Robotic Assisted Ligament Graft Placement and Tensioning," the entirety of which is incorporated herein by reference.

A robotic arm 105A may be used for holding the retractor. For example in one embodiment, the robotic arm 105A may be moved into the desired position by the surgeon. At that point, the robotic arm 105A may lock into place. In some embodiments, the robotic arm 105A is provided with data regarding the patient's position, such that if the patient moves, the robotic arm can adjust the retractor position accordingly. In some embodiments, multiple robotic arms may be used, thereby allowing multiple retractors to be held or for more than one activity to be performed simultaneously (e.g., retractor holding & reaming).

The robotic arm 105A may also be used to help stabilize the surgeon's hand while making a femoral neck cut. In this application, control of the robotic arm 105A may impose certain restrictions to prevent soft tissue damage from occurring. For example, in one embodiment, the Surgical Computer 150 tracks the position of the robotic arm 105A as it operates. If the tracked location approaches an area where tissue damage is predicted, a command may be sent to the robotic arm 105A causing it to stop. Alternatively, where the robotic arm 105A is automatically controlled by the Surgical Computer 150, the Surgical Computer may ensure that the robotic arm is not provided with any instructions that cause it to enter areas where soft tissue damage is likely to occur. The Surgical Computer 150 may impose certain restrictions on the surgeon to prevent the surgeon from reaming too far into the medial wall of the acetabulum or reaming at an incorrect angle or orientation.

In some embodiments, the robotic arm 105A may be used to hold a cup impactor at a desired angle or orientation during cup impaction. When the final position has been achieved, the robotic arm 105A may prevent any further seating to prevent damage to the pelvis.

The surgeon may use the robotic arm 105A to position the broach handle at the desired position and allow the surgeon to impact the broach into the femoral canal at the desired orientation. In some embodiments, once the Surgical Computer 150 receives feedback that the broach is fully seated, the robotic arm 105A may restrict the handle to prevent further advancement of the broach.

The robotic arm 105A may also be used for resurfacing applications. For example, the robotic arm 105A may stabilize the surgeon while using traditional instrumentation and provide certain restrictions or limitations to allow for proper placement of implant components (e.g., guide wire placement, chamfer cutter, sleeve cutter, plan cutter, etc.). Where only a burr is employed, the robotic arm 105A may stabilize the surgeon's handpiece and may impose restrictions on the handpiece to prevent the surgeon from removing unintended bone in contravention of the surgical plan.

The robotic arm 105A may be a passive arm. As an example, the robotic arm 105A may be a CIRQ robot arm available from Brainlab AG. CIRQ is a registered trademark of Brainlab AG, Olof-Palme-Str. 9 81829, München, FED REP of GERMANY. In one particular embodiment, the robotic arm 105A is an intelligent holding arm as disclosed in U.S. patent application Ser. No. 15/525,585 to Krinninger et al., U.S. patent application Ser. No. 15/561,042 to Nowatschin et al., U.S. patent application Ser. No. 15/561,048 to Nowatschin et al., and U.S. Pat. No. 10,342,636 to Nowatschin et al., the entire contents of each of which is herein incorporated by reference.

Surgical Procedure Data Generation and Collection

The various services that are provided by medical professionals to treat a clinical condition are collectively referred to as an "episode of care." For a particular surgical intervention the episode of care can include three phases: pre-operative, intra-operative, and post-operative. During each phase, data is collected or generated that can be used to analyze the episode of care in order to understand various features of the procedure and identify patterns that may be used, for example, in training models to make decisions with minimal human intervention. The data collected over the episode of care may be stored at the Surgical Computer 150 or the Surgical Data Server 180 as a complete dataset. Thus, for each episode of care, a dataset exists that comprises all of the data collectively pre-operatively about the patient, all of the data collected or stored by the CASS 100 intra-operatively, and any post-operative data provided by the patient or by a healthcare professional monitoring the patient.

As explained in further detail, the data collected during the episode of care may be used to enhance performance of the surgical procedure or to provide a holistic understanding of the surgical procedure and the patient outcomes. For example, in some embodiments, the data collected over the episode of care may be used to generate a surgical plan. In one embodiment, a high-level, pre-operative plan is refined intra-operatively as data is collected during surgery. In this way, the surgical plan can be viewed as dynamically changing in real-time or near real-time as new data is collected by the components of the CASS 100. In other embodiments, pre-operative images or other input data may be used to develop a robust plan preoperatively that is simply executed during surgery. In this case, the data collected by the CASS 100 during surgery may be used to make recommendations that ensure that the surgeon stays within the pre-operative surgical plan. For example, if the surgeon is unsure how to achieve a certain prescribed cut or implant alignment, the Surgical Computer 150 can be queried for a recommendation. In still other embodiments, the pre-operative and intra-operative planning approaches can be combined such that a robust pre-operative plan can be dynamically modified, as necessary or desired, during the surgical procedure. In some embodiments, a biomechanics-based model of patient anatomy contributes simulation data to be considered by the CASS 100 in developing preoperative, intraoperative, and post-operative/rehabilitation procedures to optimize implant performance outcomes for the patient.

Aside from changing the surgical procedure itself, the data gathered during the episode of care may be used as an input to other procedures ancillary to the surgery. For example, in some embodiments, implants can be designed using episode of care data. Example data-driven techniques for designing, sizing, and fitting implants are described in U.S. patent application Ser. No. 13/814,531 filed Aug. 15, 2011 and entitled "Systems and Methods for Optimizing Parameters for Orthopaedic Procedures"; U.S. patent application Ser. No. 14/232,958 filed Jul. 20, 2012 and entitled "Systems and Methods for Optimizing Fit of an Implant to Anatomy"; and U.S. patent application Ser. No. 12/234,444 filed Sep. 19, 2008 and entitled "Operatively Tuning Implants for Increased Performance," the entire contents of each of which are hereby incorporated by reference into this patent application.

Furthermore, the data can be used for educational, training, or research purposes. For example, using the network-based approach described below in FIG. 5C, other doctors or students can remotely view surgeries in interfaces that allow them to selectively view data as it is collected from the various components of the CASS 100. After the surgical procedure, similar interfaces may be used to "playback" a surgery for training or other educational purposes, or to identify the source of any issues or complications with the procedure.

Data acquired during the pre-operative phase generally includes all information collected or generated prior to the surgery. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The pre-operative data may also include images related to the anatomical area of interest. These images may be captured, for example, using Magnetic Resonance Imaging (MRI), Computed Tomography (CT), X-ray, ultrasound, or any other modality known in the art. The pre-operative data may also comprise quality of life data captured from the patient. For example, in one embodiment, pre-surgery patients use a mobile application ("app") to answer questionnaires regarding their current quality of life. In some embodiments, preoperative data used by the CASS 100 includes demographic, anthropometric, cultural, or other specific traits about a patient that can coincide with activity levels and specific patient activities to customize the surgical plan to the patient. For example, certain cultures or demographics may be more likely to use a toilet that requires squatting on a daily basis.

Figure 5A:
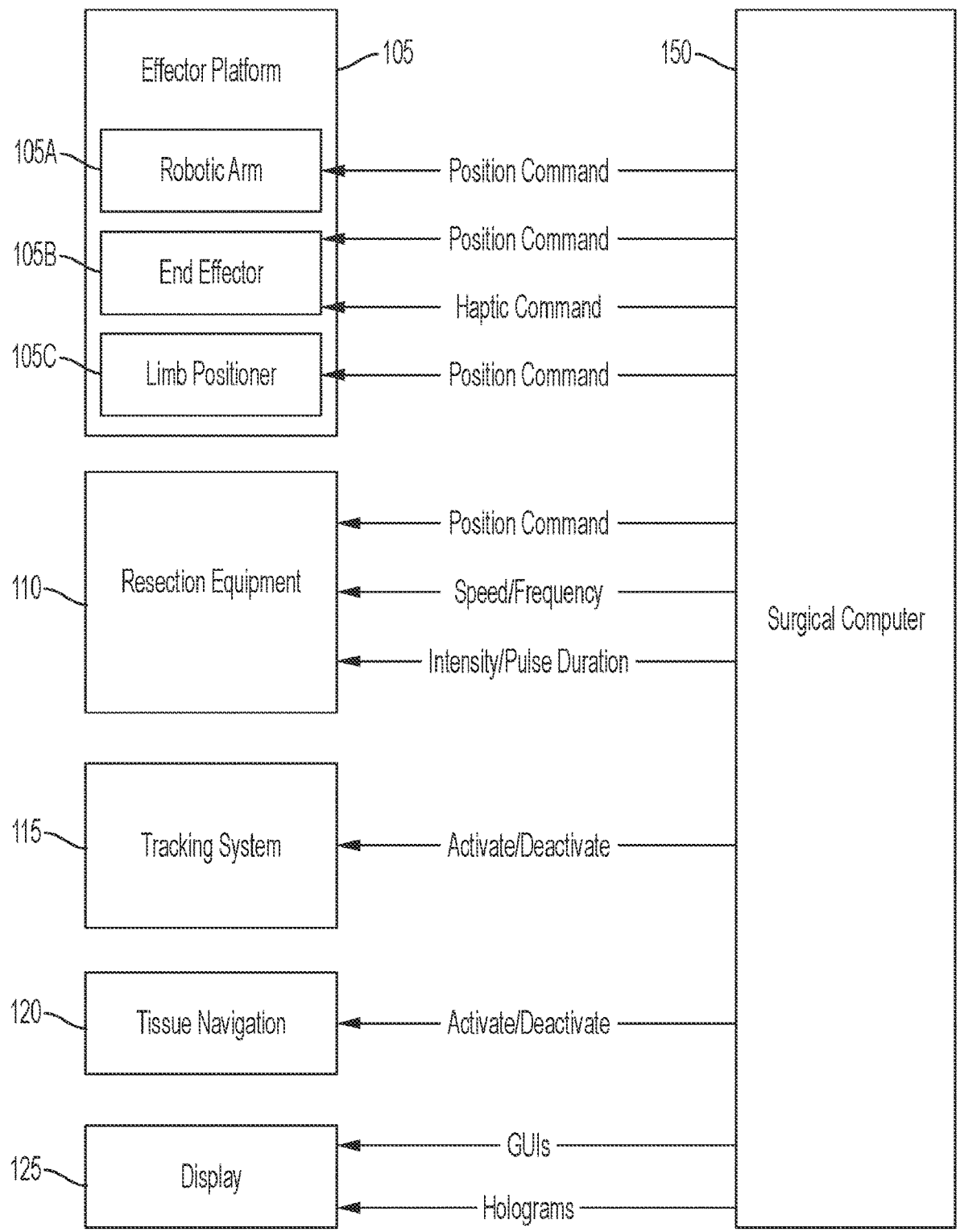
FIG. 5A depicts illustrative control instructions that a surgical computer provides to other components of a CASS in accordance with an embodiment.
Figure 5B:
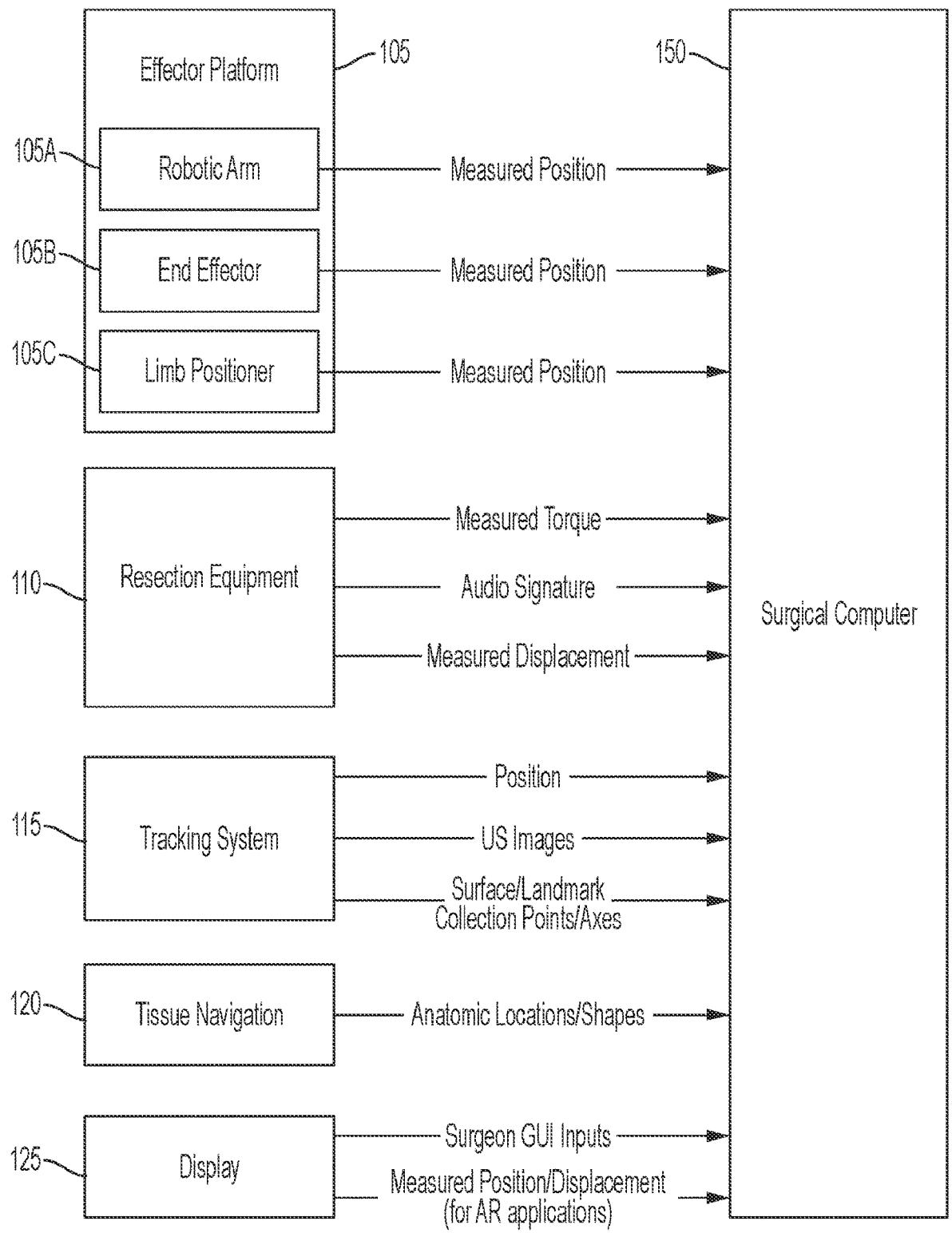
FIG. 5B depicts illustrative control instructions that components of a CASS provide to a surgical computer in accordance with an embodiment.

FIGS. 5A and 5B provide examples of data that may be acquired during the intra-operative phase of an episode of care. These examples are based on the various components of the CASS 100 described above with reference to FIG. 1; however, it should be understood that other types of data may be used based on the types of equipment used during surgery and their use.

FIG. 5A shows examples of some of the control instructions that the Surgical Computer 150 provides to other components of the CASS 100, according to some embodiments. Note that the example of FIG. 5A assumes that the components of the Effector Platform 105 are each controlled directly by the Surgical Computer 150. In embodiments where a component is manually controlled by the Surgeon 111, instructions may be provided on the Display 125 or AR HMD 155 instructing the Surgeon 111 how to move the component.

The various components included in the Effector Platform 105 are controlled by the Surgical Computer 150 providing position commands that instruct the component where to move within a coordinate system. In some embodiments, the Surgical Computer 150 provides the Effector Platform 105 with instructions defining how to react when a component of the Effector Platform 105 deviates from a surgical plan. These commands are referenced in FIG. 5A as "haptic" commands. For example, the End Effector 105B may provide a force to resist movement outside of an area where resection is planned. Other commands that may be used by the Effector Platform 105 include vibration and audio cues.

In some embodiments, the end effectors 105B of the robotic arm 105A are operatively coupled with cutting guide 105D. In response to an anatomical model of the surgical scene, the robotic arm 105A can move the end effectors 105B and the cutting guide 105D into position to match the location of the femoral or tibial cut to be performed in accordance with the surgical plan. This can reduce the likelihood of error, allowing the vision system and a processor utilizing that vision system to implement the surgical plan to place a cutting guide 105D at the precise location and orientation relative to the tibia or femur to align a cutting slot of the cutting guide with the cut to be performed according to the surgical plan. Then, a surgeon can use any suitable tool, such as an oscillating or rotating saw or drill to perform the cut (or drill a hole) with perfect placement and orientation because the tool is mechanically limited by the features of the cutting guide 105D. In some embodiments, the cutting guide 105D may include one or more pin holes that are used by a surgeon to drill and screw or pin the cutting guide into place before performing a resection of the patient tissue using the cutting guide. This can free the robotic arm 105A or ensure that the cutting guide 105D is fully affixed without moving relative to the bone to be resected. For example, this procedure can be used to make the first distal cut of the femur during a total knee arthroplasty. In some embodiments, where the arthroplasty is a hip arthroplasty, cutting guide 105D can be fixed to the femoral head or the acetabulum for the respective hip arthroplasty resection. It should be understood that any arthroplasty that utilizes precise cuts can use the robotic arm 105A and/or cutting guide 105D in this manner.

The Resection Equipment 110 is provided with a variety of commands to perform bone or tissue operations. As with the Effector Platform 105, position information may be provided to the Resection Equipment 110 to specify where it should be located when performing resection. Other commands provided to the Resection Equipment 110 may be dependent on the type of resection equipment. For example, for a mechanical or ultrasonic resection tool, the commands may specify the speed and frequency of the tool. For Radiofrequency Ablation (RFA) and other laser ablation tools, the commands may specify intensity and pulse duration.

Some components of the CASS 100 do not need to be directly controlled by the Surgical Computer 150; rather, the Surgical Computer 150 only needs to activate the component, which then executes software locally specifying the manner in which to collect data and provide it to the Surgical Computer 150. In the example of FIG. 5A, there are two components that are operated in this manner: the Tracking System 115 and the Tissue Navigation System 120.

The Surgical Computer 150 provides the Display 125 with any visualization that is needed by the Surgeon 111 during surgery. For monitors, the Surgical Computer 150 may provide instructions for displaying images, GUIs, etc. using techniques known in the art. The display 125 can include various portions of the workflow of a surgical plan. During the registration process, for example, the display 125 can show a preoperatively constructed 3D bone model and depict the locations of the probe as the surgeon uses the probe to collect locations of anatomical landmarks on the patient. The display 125 can include information about the surgical target area. For example, in connection with a TKA, the display 125 can depict the mechanical and anatomical axes of the femur and tibia. The display 125 can depict varus and valgus angles for the knee joint based on a surgical plan, and the CASS 100 can depict how such angles will be affected if contemplated revisions to the surgical plan are made. Accordingly, the display 125 is an interactive interface that can dynamically update and display how changes to the surgical plan would impact the procedure and the final position and orientation of implants installed on bone.

As the workflow progresses to preparation of bone cuts or resections, the display 125 can depict the planned or recommended bone cuts before any cuts are performed. The surgeon 111 can manipulate the image display to provide different anatomical perspectives of the target area and can have the option to alter or revise the planned bone cuts based on intraoperative evaluation of the patient. The display 125 can depict how the chosen implants would be installed on the bone if the planned bone cuts are performed. If the surgeon 111 choses to change the previously planned bone cuts, the display 125 can depict how the revised bone cuts would change the position and orientation of the implant when installed on the bone.

The display 125 can provide the surgeon 111 with a variety of data and information about the patient, the planned surgical intervention, and the implants. Various patient-specific information can be displayed, including real-time data concerning the patient's health such as heart rate, blood pressure, etc. The display 125 also can include information about the anatomy of the surgical target region including the location of landmarks, the current state of the anatomy (e.g., whether any resections have been made, the depth and angles of planned and executed bone cuts), and future states of the anatomy as the surgical plan progresses. The display 125 also can provide or depict additional information about the surgical target region. For a TKA, the display 125 can provide information about the gaps (e.g., gap balancing) between the femur and tibia and how such gaps will change if the planned surgical plan is carried out. For a TKA, the display 125 can provide additional relevant information about the knee joint such as data about the joint's tension (e.g., ligament laxity) and information concerning rotation and alignment of the joint. The display 125 can depict how the planned implants' locations and positions will affect the patient as the knee joint is flexed. The display 125 can depict how the use of different implants or the use of different sizes of the same implant will affect the surgical plan and preview how such implants will be positioned on the bone. The CASS 100 can provide such information for each of the planned bone resections in a TKA or THA. In a TKA, the CASS 100 can provide robotic control for one or more of the planned bone resections. For example, the CASS 100 can provide robotic control only for the initial distal femur cut, and the surgeon 111 can manually perform other resections (anterior, posterior and chamfer cuts) using conventional means, such as a 4-in-1 cutting guide or jig 105D.

The display 125 can employ different colors to inform the surgeon of the status of the surgical plan. For example, un-resected bone can be displayed in a first color, resected bone can be displayed in a second color, and planned resections can be displayed in a third color. Implants can be superimposed onto the bone in the display 125, and implant colors can change or correspond to different types or sizes of implants.

The information and options depicted on the display 125 can vary depending on the type of surgical procedure being performed. Further, the surgeon 111 can request or select a particular surgical workflow display that matches or is consistent with his or her surgical plan preferences. For example, for a surgeon 111 who typically performs the tibial cuts before the femoral cuts in a TKA, the display 125 and associated workflow can be adapted to take this preference into account. The surgeon 111 also can preselect that certain steps be included or deleted from the standard surgical workflow display. For example, if a surgeon 111 uses resection measurements to finalize an implant plan but does not analyze ligament gap balancing when finalizing the implant plan, the surgical workflow display can be organized into modules, and the surgeon can select which modules to display and the order in which the modules are provided based on the surgeon's preferences or the circumstances of a particular surgery. Modules directed to ligament and gap balancing, for example, can include pre- and post-resection ligament/gap balancing, and the surgeon 111 can select which modules to include in their default surgical plan workflow depending on whether they perform such ligament and gap balancing before or after (or both) bone resections are performed.

For more specialized display equipment, such as AR HMDs, the Surgical Computer 150 may provide images, text, etc. using the data format supported by the equipment. For example, if the Display 125 is a holography device such as the Microsoft HoloLens™ or Magic Leap One™, the Surgical Computer 150 may use the HoloLens Application Program Interface (API) to send commands specifying the position and content of holograms displayed in the field of view of the Surgeon 111.

In some embodiments, one or more surgical planning models may be incorporated into the CASS 100 and used in the development of the surgical plans provided to the surgeon 111. The term "surgical planning model" refers to software that simulates the biomechanics performance of anatomy under various scenarios to determine the optimal way to perform cutting and other surgical activities. For example, for knee replacement surgeries, the surgical planning model can measure parameters for functional activities, such as deep knee bends, gait, etc., and select cut locations on the knee to optimize implant placement. One example of a surgical planning model is the LIFEMOD™ simulation software from SMITH AND NEPHEW, INC. In some embodiments, the Surgical Computer 150 includes computing architecture that allows full execution of the surgical planning model during surgery (e.g., a GPU-based parallel processing environment). In other embodiments, the Surgical Computer 150 may be connected over a network to a remote computer that allows such execution, such as a Surgical Data Server 180 (see FIG. 5C). As an alternative to full execution of the surgical planning model, in some embodiments, a set of transfer functions are derived that simplify the mathematical operations captured by the model into one or more predictor equations. Then, rather than execute the full simulation during surgery, the predictor equations are used. Further details on the use of transfer functions are described in WIPO Publication No. 2020/037308, filed Aug. 19, 2019, entitled "Patient Specific Surgical Method and System," the entirety of which is incorporated herein by reference.

FIG. 5B shows examples of some of the types of data that can be provided to the Surgical Computer 150 from the various components of the CASS 100. In some embodiments, the components may stream data to the Surgical Computer 150 in real-time or near real-time during surgery. In other embodiments, the components may queue data and send it to the Surgical Computer 150 at set intervals (e.g., every second). Data may be communicated using any format known in the art. Thus, in some embodiments, the components all transmit data to the Surgical Computer 150 in a common format. In other embodiments, each component may use a different data format, and the Surgical Computer 150 is configured with one or more software applications that enable translation of the data.

In general, the Surgical Computer 150 may serve as the central point where CASS data is collected. The exact content of the data will vary depending on the source. For example, each component of the Effector Platform 105 provides a measured position to the Surgical Computer 150. Thus, by comparing the measured position to a position originally specified by the Surgical Computer 150 (see FIG. 5B), the Surgical Computer can identify deviations that take place during surgery.

The Resection Equipment 110 can send various types of data to the Surgical Computer 150 depending on the type of equipment used. Example data types that may be sent include the measured torque, audio signatures, and measured displacement values. Similarly, the Tracking Technology 115 can provide different types of data depending on the tracking methodology employed. Example tracking data types include position values for tracked items (e.g., anatomy, tools, etc.), ultrasound images, and surface or landmark collection points or axes. The Tissue Navigation System 120 provides the Surgical Computer 150 with anatomic locations, shapes, etc. as the system operates.

Although the Display 125 generally is used for outputting data for presentation to the user, it may also provide data to the Surgical Computer 150. For example, for embodiments where a monitor is used as part of the Display 125, the Surgeon 111 may interact with a GUI to provide inputs which are sent to the Surgical Computer 150 for further processing. For AR applications, the measured position and displacement of the HMD may be sent to the Surgical Computer 150 so that it can update the presented view as needed.

During the post-operative phase of the episode of care, various types of data can be collected to quantify the overall improvement or deterioration in the patient's condition as a result of the surgery. The data can take the form of, for example, self-reported information reported by patients via questionnaires. For example, in the context of a knee replacement surgery, functional status can be measured with an Oxford Knee Score questionnaire, and the post-operative quality of life can be measured with a EQ5D-5L questionnaire. Other examples in the context of a hip replacement surgery may include the Oxford Hip Score, Harris Hip Score, and WOMAC (Western Ontario and McMaster Universities Osteoarthritis index). Such questionnaires can be administered, for example, by a healthcare professional directly in a clinical setting or using a mobile app that allows the patient to respond to questions directly. In some embodiments, the patient may be outfitted with one or more wearable devices that collect data relevant to the surgery. For example, following a knee surgery, the patient may be outfitted with a knee brace that includes sensors that monitor knee positioning, flexibility, etc. This information can be collected and transferred to the patient's mobile device for review by the surgeon to evaluate the outcome of the surgery and address any issues. In some embodiments, one or more cameras can capture and record the motion of a patient's body segments during specified activities postoperatively.

This motion capture can be compared to a biomechanics model to better understand the functionality of the patient's joints and better predict progress in recovery and identify any possible revisions that may be needed.

The post-operative stage of the episode of care can continue over the entire life of a patient. For example, in some embodiments, the Surgical Computer 150 or other components comprising the CASS 100 can continue to receive and collect data relevant to a surgical procedure after the procedure has been performed. This data may include, for example, images, answers to questions, "normal" patient data (e.g., blood type, blood pressure, conditions, medications, etc.), biometric data (e.g., gait, etc.), and objective and subjective data about specific issues (e.g., knee or hip joint pain). This data may be explicitly provided to the Surgical Computer 150 or other CASS component by the patient or the patient's physician(s). Alternatively or additionally, the Surgical Computer 150 or other CASS component can monitor the patient's EMR and retrieve relevant information as it becomes available. This longitudinal view of the patient's recovery allows the Surgical Computer 150 or other CASS component to provide a more objective analysis of the patient's outcome to measure and track success or lack of success for a given procedure. For example, a condition experienced by a patient long after the surgical procedure can be linked back to the surgery through a regression analysis of various data items collected during the episode of care. This analysis can be further enhanced by performing the analysis on groups of patients that had similar procedures and/or have similar anatomies.

In some embodiments, data is collected at a central location to provide for easier analysis and use. Data can be manually collected from various CASS components in some instances. For example, a portable storage device (e.g., USB stick) can be attached to the Surgical Computer 150 into order to retrieve data collected during surgery. The data can then be transferred, for example, via a desktop computer to the centralized storage. Alternatively, in some embodiments, the Surgical Computer 150 is connected directly to the centralized storage via a Network 175 as shown in FIG. 5C.

Figure 5C:
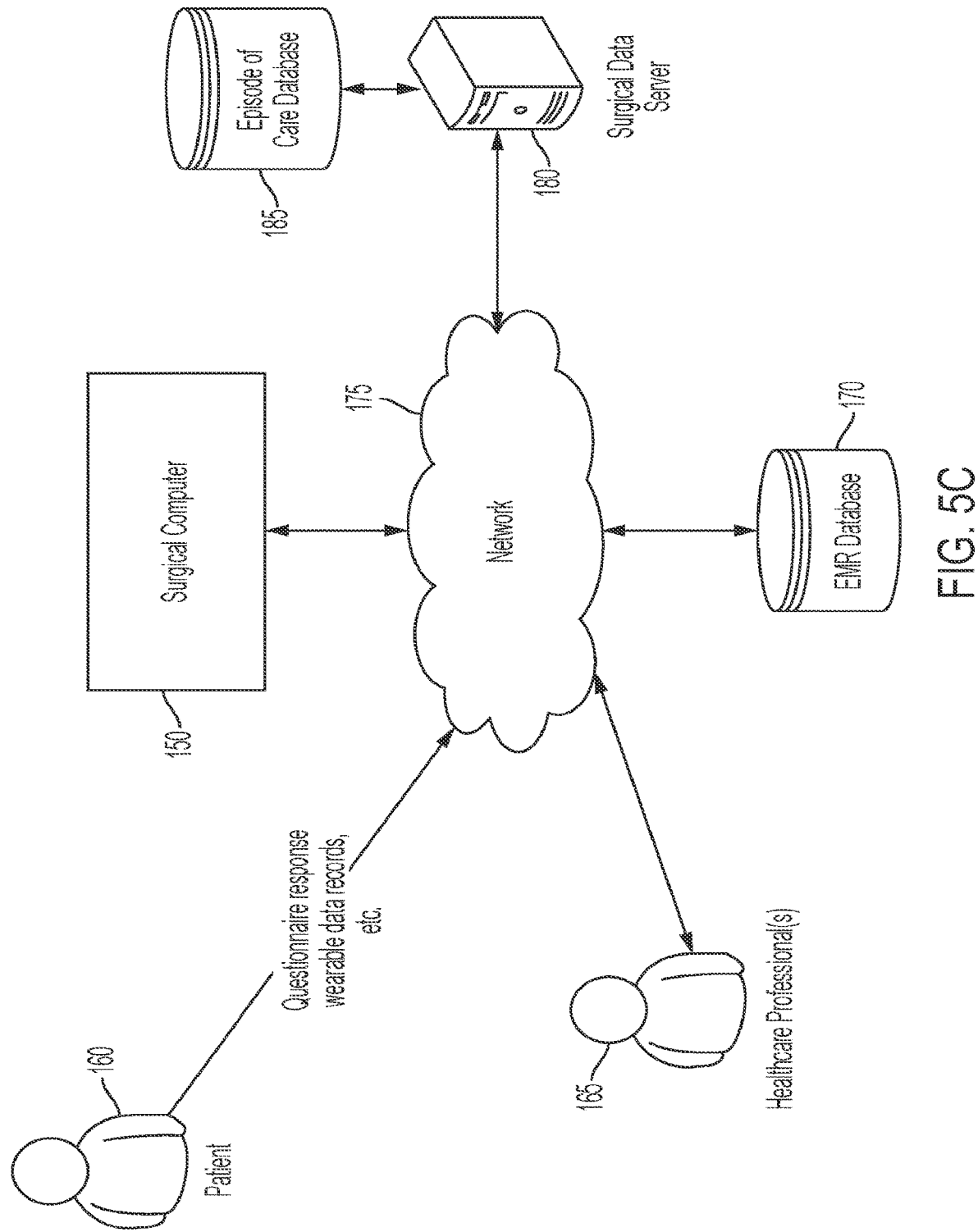
FIG. 5C depicts an illustrative implementation in which a surgical computer is connected to a surgical data server via a network in accordance with an embodiment.

FIG. 5C illustrates a "cloud-based" implementation in which the Surgical Computer 150 is connected to a Surgical Data Server 180 via a Network 175. This Network 175 may be, for example, a private intranet or the Internet. In addition to the data from the Surgical Computer 150, other sources can transfer relevant data to the Surgical Data Server 180. The example of FIG. 5C shows 3 additional data sources: the Patient 160, Healthcare Professional(s) 165, and an EMR Database 170. Thus, the Patient 160 can send pre-operative and post-operative data to the Surgical Data Server 180, for example, using a mobile app. The Healthcare Professional(s) 165 includes the surgeon and his or her staff as well as any other professionals working with Patient 160 (e.g., a personal physician, a rehabilitation specialist, etc.). It should also be noted that the EMR Database 170 may be used for both pre-operative and post-operative data. For example, assuming that the Patient 160 has given adequate permissions, the Surgical Data Server 180 may collect the EMR of the Patient pre-surgery. Then, the Surgical Data Server 180 may continue to monitor the EMR for any updates post-surgery.

At the Surgical Data Server 180, an Episode of Care Database 185 is used to store the various data collected over a patient's episode of care. The Episode of Care Database 185 may be implemented using any technique known in the art. For example, in some embodiments, a SQL-based database may be used where all of the various data items are structured in a manner that allows them to be readily incorporated in two SQL's collection of rows and columns. However, in other embodiments a No-SQL database may be employed to allow for unstructured data, while providing the ability to rapidly process and respond to queries. As is understood in the art, the term "No-SQL" is used to define a class of data stores that are non-relational in their design. Various types of No-SQL databases may generally be grouped according to their underlying data model. These groupings may include databases that use column-based data models (e.g., Cassandra), document-based data models (e.g., MongoDB), key-value based data models (e.g., Redis), and/or graph-based data models (e.g., Allego). Any type of No-SQL database may be used to implement the various embodiments described herein and, in some embodiments, the different types of databases may support the Episode of Care Database 185.

Data can be transferred between the various data sources and the Surgical Data Server 180 using any data format and transfer technique known in the art. It should be noted that the architecture shown in FIG. 5C allows transmission from the data source to the Surgical Data Server 180, as well as retrieval of data from the Surgical Data Server 180 by the data sources. For example, as explained in detail below, in some embodiments, the Surgical Computer 150 may use data from past surgeries, machine learning models, etc. to help guide the surgical procedure.

In some embodiments, the Surgical Computer 150 or the Surgical Data Server 180 may execute a de-identification process to ensure that data stored in the Episode of Care Database 185 meets Health Insurance Portability and Accountability Act (HIPAA) standards or other requirements mandated by law. HIPAA provides a list of certain identifiers that must be removed from data during de-identification. The aforementioned de-identification process can scan for these identifiers in data that is transferred to the Episode of Care Database 185 for storage. For example, in one embodiment, the Surgical Computer 150 executes the de-identification process just prior to initiating transfer of a particular data item or set of data items to the Surgical Data Server 180. In some embodiments, a unique identifier is assigned to data from a particular episode of care to allow for re-identification of the data if necessary.

Although FIGS. 5A - 5C discuss data collection in the context of a single episode of care, it should be understood that the general concept can be extended to data collection from multiple episodes of care. For example, surgical data may be collected over an entire episode of care each time a surgery is performed with the CASS 100 and stored at the Surgical Computer 150 or at the Surgical Data Server 180. As explained in further detail below, a robust database of episode of care data allows the generation of optimized values, measurements, distances, or other parameters and other recommendations related to the surgical procedure. In some embodiments, the various datasets are indexed in the database or other storage medium in a manner that allows for rapid retrieval of relevant information during the surgical procedure. For example, in one embodiment, a patient-centric set of indices may be used so that data pertaining to a particular patient or a set of patients similar to a particular patient can be readily extracted. This concept can be similarly applied to surgeons, implant characteristics, CASS component versions, etc.

Further details of the management of episode of care data is described in U.S. Patent Application No. 62/783,858 filed Dec. 21, 2018 and entitled "Methods and Systems for Providing an Episode of Care," the entirety of which is incorporated herein by reference.

Open Versus Closed Digital Ecosystems

In some embodiments, the CASS 100 is designed to operate as a self-contained or "closed" digital ecosystem. Each component of the CASS 100 is specifically designed to be used in the closed ecosystem, and data is generally not accessible to devices outside of the digital ecosystem. For example, in some embodiments, each component includes software or firmware that implements proprietary protocols for activities such as communication, storage, security, etc. The concept of a closed digital ecosystem may be desirable for a company that wants to control all components of the CASS 100 to ensure that certain compatibility, security, and reliability standards are met. For example, the CASS 100 can be designed such that a new component cannot be used with the CASS unless it is certified by the company.

In other embodiments, the CASS 100 is designed to operate as an "open" digital ecosystem. In these embodiments, components may be produced by a variety of different companies according to standards for activities, such as communication, storage, and security. Thus, by using these standards, any company can freely build an independent, compliant component of the CASS platform. Data may be transferred between components using publicly available application programming interfaces (APIs) and open, shareable data formats.

To illustrate one type of recommendation that may be performed with the CASS 100, a technique for optimizing surgical parameters is disclosed below. The term "optimization" in this context means selection of parameters that are optimal based on certain specified criteria. In an extreme case, optimization can refer to selecting optimal parameter(s) based on data from the entire episode of care, including any pre-operative data, the state of CASS data at a given point in time, and post-operative goals. Moreover, optimization may be performed using historical data, such as data generated during past surgeries involving, for example, the same surgeon, past patients with physical characteristics similar to the current patient, or the like.

The optimized parameters may depend on the portion of the patient's anatomy to be operated on. For example, for knee surgeries, the surgical parameters may include positioning information for the femoral and tibial component including, without limitation, rotational alignment (e.g., varus/valgus rotation, external rotation, flexion rotation for the femoral component, posterior slope of the tibial component), resection depths (e.g., varus knee, valgus knee), and implant type, size and position. The positioning information may further include surgical parameters for the combined implant, such as overall limb alignment, combined tibiofemoral hyperextension, and combined tibiofemoral resection. Additional examples of parameters that could be optimized for a given TKA femoral implant by the CASS 100 include the following:

| Parameter | Reference | Exemplary Recommendation (s) |
| --- | --- | --- |
| Size | Posterior | The largest sized implant that does not overhang medial/lateral bone edges or overhang the anterior femur.<br>A size that does not result in overstuffing the patella femoral joint |
| Implant Position-Medial Lateral | Medial/lateral cortical bone edges | Center the implant evenly between the medial/lateral cortical bone edges |
| Resection Depth-Varus Knee | Distal and posterior lateral | 6 mm of bone |
| Resection Depth-Valgus Knee | Distal and posterior medial | 7 mm of bone |
| Rotation-Varus/Valgus | Mechanical Axis | 1° varus |
| Rotation-External | Transepicondylar Axis | 1° external from the transepicondylar axis |
| Rotation-Flexion | Mechanical Axis | 3° flexed |

Additional examples of parameters that could be optimized for a given TKA tibial implant by the CASS 100 include the following:

| Parameter | Reference | Exemplary Recommendation (s) |
| --- | --- | --- |
| Size | Posterior | The largest sized implant that does not overhang the medial, lateral, anterior, and posterior tibial edges |
| Implant Position | Medial/lateral and anterior/posterior cortical bone edges | Center the implant evenly between the medial/lateral and anterior/posterior cortical bone edges |
| Resection Depth-Varus Knee | Lateral/Medial | 4 mm of bone |
| Resection Depth-Valgus Knee | Lateral/Medial | 5 mm of bone |
| Rotation-Varus/Valgus | Mechanical Axis | 1° valgus |
| Rotation-External | Tibial Anterior Posterior Axis | 1° external from the tibial anterior paxis |
| Posterior Slope | Mechanical Axis | 3° posterior slope |

For hip surgeries, the surgical parameters may comprise femoral neck resection location and angle, cup inclination angle, cup anteversion angle, cup depth, femoral stem design, femoral stem size, fit of the femoral stem within the canal, femoral offset, leg length, and femoral version of the implant.

Shoulder parameters may include, without limitation, humeral resection depth/angle, humeral stem version, humeral offset, glenoid version and inclination, as well as reverse shoulder parameters such as humeral resection depth/angle, humeral stem version, Glenoid tilt/version, glenosphere orientation, glenosphere offset and offset direction.

Various conventional techniques exist for optimizing surgical parameters. However, these techniques are typically computationally intensive and, thus, parameters often need to be determined pre-operatively. As a result, the surgeon is limited in his or her ability to make modifications to optimized parameters based on issues that may arise during surgery. Moreover, conventional optimization techniques typically operate in a "black box" manner with little or no explanation regarding recommended parameter values. Thus, if the surgeon decides to deviate from a recommended parameter value, the surgeon typically does so without a full understanding of the effect of that deviation on the rest of the surgical workflow, or the impact of the deviation on the patient's post-surgery quality of life.

Operative Patient Care System

Figure 6:
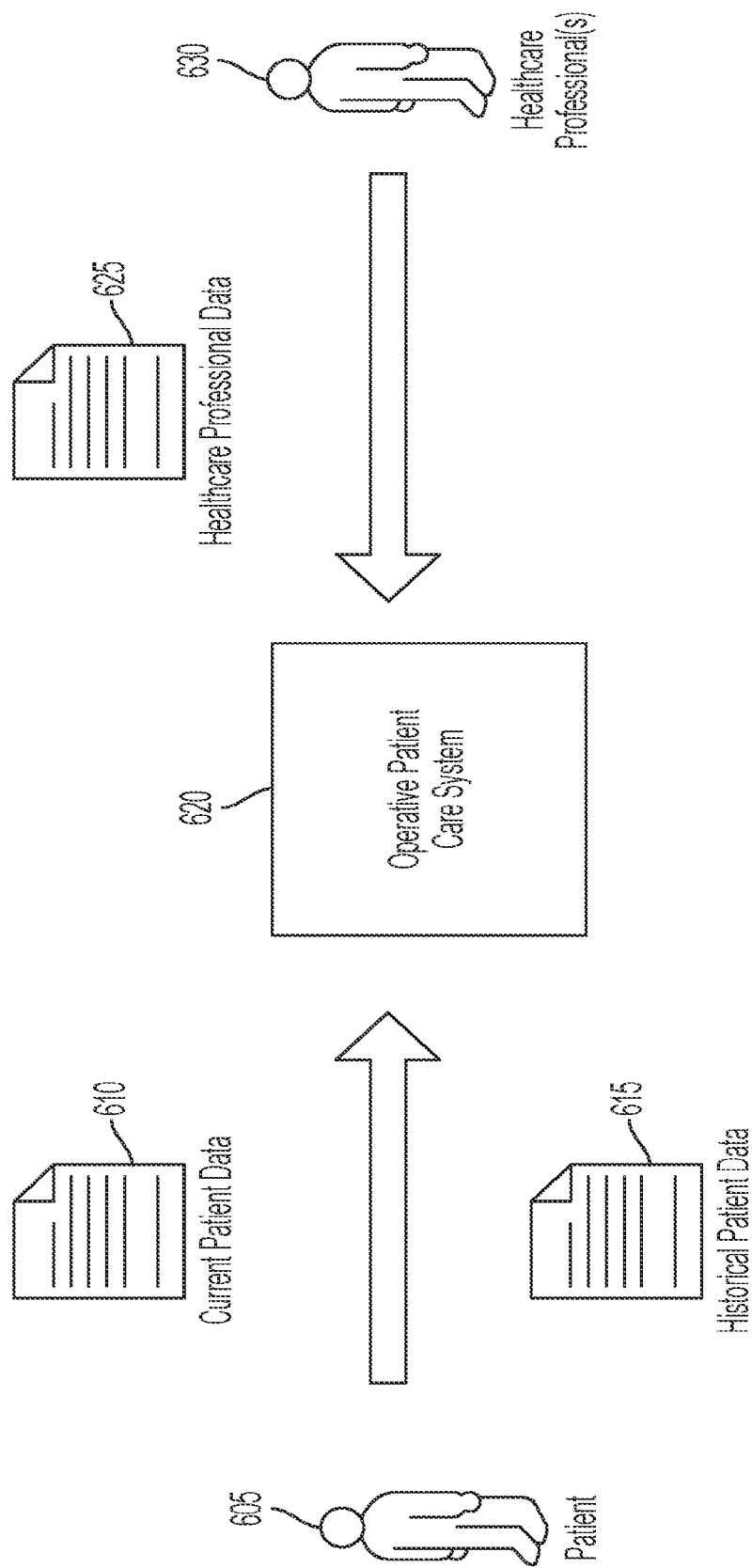
FIG. 6 depicts an operative patient care system and illustrative data sources in accordance with an embodiment.

The general concepts of optimization may be extended to the entire episode of care using an Operative Patient Care System 620 that uses the surgical data, and other data from the Patient 605 and Healthcare Professionals 630 to optimize outcomes and patient satisfaction as depicted in FIG. 6.

Conventionally, pre-operative diagnosis, pre-operative surgical planning, intra-operative execution of a prescribed plan, and post-operative management of total joint arthroplasty are based on individual experience, published literature, and training knowledge bases of surgeons (ultimately, tribal knowledge of individual surgeons and their 'network' of peers and journal publications) and their native ability to make accurate intra-operative tactile discernment of "balance" and accurate manual execution of planar resections using guides and visual cues. This existing knowledge base and execution is limited with respect to the outcomes optimization offered to patients needing care. For example, limits exist with respect to accurately diagnosing a patient to the proper, least-invasive prescribed care; aligning dynamic patient, healthcare economic, and surgeon preferences with patient-desired outcomes; executing a surgical plan resulting in proper bone alignment and balance, etc .; and receiving data from disconnected sources having different biases that are difficult to reconcile into a holistic patient framework. Accordingly, a data-driven tool that more accurately models anatomical response and guides the surgical plan can improve the existing approach.

The Operative Patient Care System 620 is designed to utilize patient specific data, surgeon data, healthcare facility data, and historical outcome data to develop an algorithm that suggests or recommends an optimal overall treatment plan for the patient's entire episode of care (preoperative, operative, and postoperative) based on a desired clinical outcome. For example, in one embodiment, the Operative Patient Care System 620 tracks adherence to the suggested or recommended plan, and adapts the plan based on patient/care provider performance. Once the surgical treatment plan is complete, collected data is logged by the Operative Patient Care System 620 in a historical database. This database is accessible for future patients and the development of future treatment plans. In addition to utilizing statistical and mathematical models, simulation tools (e.g., LIFEMOD®) can be used to simulate outcomes, alignment, kinematics, etc. based on a preliminary or proposed surgical plan, and reconfigure the preliminary or proposed plan to achieve desired or optimal results according to a patient's profile or a surgeon's preferences. The Operative Patient Care System 620 ensures that each patient is receiving personalized surgical and rehabilitative care, thereby improving the chance of successful clinical outcomes and lessening the economic burden on the facility associated with near-term revision.

In some embodiments, the Operative Patient Care System 620 employs a data collecting and management method to provide a detailed surgical case plan with distinct steps that are monitored and/or executed using a CASS 100. The performance of the user(s) is calculated at the completion of each step and can be used to suggest changes to the subsequent steps of the case plan. Case plan generation relies on a series of input data that is stored on a local or cloud-storage database. Input data can be related to both the current patient undergoing treatment and historical data from patients who have received similar treatment(s).

A Patient 605 provides inputs such as Current Patient Data 610 and Historical Patient Data 615 to the Operative Patient Care System 620. Various methods generally known in the art may be used to gather such inputs from the Patient 605. For example, in some embodiments, the Patient 605 fills out a paper or digital survey that is parsed by the Operative Patient Care System 620 to extract patient data. In other embodiments, the Operative Patient Care System 620 may extract patient data from existing information sources, such as electronic medical records (EMRs), health history files, and payer/provider historical files. In still other embodiments, the Operative Patient Care System 620 may provide an application program interface (API) that allows the external data source to push data to the Operative Patient Care System. For example, the Patient 605 may have a mobile phone, wearable device, or other mobile device that collects data (e.g., heart rate, pain or discomfort levels, exercise or activity levels, or patient-submitted responses to the patient's adherence with any number of pre-operative plan criteria or conditions) and provides that data to the Operative Patient Care System 620. Similarly, the Patient 605 may have a digital application on his or her mobile or wearable device that enables data to be collected and transmitted to the Operative Patient Care System 620.

Current Patient Data 610 can include, but is not limited to, activity level, preexisting conditions, comorbidities, prehab performance, health and fitness level, pre-operative expectation level (relating to hospital, surgery, and recovery), a Metropolitan Statistical Area (MSA) driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels of pain or discomfort, care infrastructure information (payer coverage type, home health care infrastructure level, etc.), and an indication of the expected ideal outcome of the procedure.

Historical Patient Data 615 can include, but is not limited to, activity level, preexisting conditions, comorbidities, prehab performance, health and fitness level, pre-operative expectation level (relating to hospital, surgery, and recovery), a MSA driven score, genetic background, prior injuries (sports, trauma, etc.), previous joint arthroplasty, previous trauma procedures, previous sports medicine procedures, treatment of the contralateral joint or limb, gait or biomechanical information (back and ankle issues), levels or pain or discomfort, care infrastructure information (payer coverage type, home health care infrastructure level, etc.), expected ideal outcome of the procedure, actual outcome of the procedure (patient reported outcomes [PROs], survivorship of implants, pain levels, activity levels, etc.), sizes of implants used, position/orientation/alignment of implants used, soft-tissue balance achieved, etc.

Healthcare Professional(s) 630 conducting the procedure or treatment may provide various types of data 625 to the Operative Patient Care System 620. This Healthcare Professional Data 625 may include, for example, a description of a known or preferred surgical technique (e.g., Cruciate Retaining (CR) vs Posterior Stabilized (PS), up- vs downsizing, tourniquet vs tourniquet-less, femoral stem style, preferred approach for THA, etc.), the level of training of the Healthcare Professional(s) 630 (e.g., years in practice, fellowship trained, where they trained, whose techniques they emulate), previous success level including historical data (outcomes, patient satisfaction), and the expected ideal outcome with respect to range of motion, days of recovery, and survivorship of the device. The Healthcare Professional Data 625 can be captured, for example, with paper or digital surveys provided to the Healthcare Professional 630, via inputs to a mobile application by the Healthcare Professional, or by extracting relevant data from EMRs. In addition, the CASS 100 may provide data such as profile data (e.g., a Patient Specific Knee Instrument Profile) or historical logs describing use of the CASS during surgery.

Information pertaining to the facility where the procedure or treatment will be conducted may be included in the input data. This data can include, without limitation, the following: Ambulatory Surgery Center (ASC) vs hospital, facility trauma level, Comprehensive Care for Joint Replacement Program (CJR) or bundle candidacy, a MSA driven score, community vs metro, academic vs non-academic, postoperative network access (Skilled Nursing Facility [SNF] only, Home Health, etc.), availability of medical professionals, implant availability, and availability of surgical equipment.

These facility inputs can be captured by, for example and without limitation, Surveys (Paper/Digital), Surgery Scheduling Tools (e.g., apps, Websites, Electronic Medical Records [EMRs], etc.), Databases of Hospital Information (on the Internet), etc. Input data relating to the associated healthcare economy including, but not limited to, the socioeconomic profile of the patient, the expected level of reimbursement the patient will receive, and if the treatment is patient specific may also be captured.

These healthcare economic inputs can be captured by, for example and without limitation, Surveys (Paper/Digital), Direct Payer Information, Databases of Socioeconomic status (on the Internet with zip code), etc. Finally, data derived from simulation of the procedure is captured. Simulation inputs include implant size, position, and orientation. Simulation can be conducted with custom or commercially available anatomical modeling software programs (e.g., LIFEMODR, AnyBody, or OpenSIM). It is noted that the data inputs described above may not be available for every patient, and the treatment plan will be generated using the data that is available.

Prior to surgery, the Patient Data 610, 615 and Healthcare Professional Data 625 may be captured and stored in a cloud-based or online database (e.g., the Surgical Data Server 180 shown in FIG. 5C). Information relevant to the procedure is supplied to a computing system via wireless data transfer or manually with the use of portable media storage. The computing system is configured to generate a case plan for use with a CASS 100. Case plan generation will be described hereinafter. It is noted that the system has access to historical data from previous patients undergoing treatment, including implant size, placement, and orientation as generated by a computer-assisted, patient-specific knee instrument (PSKI) selection system, or automatically by the CASS 100 itself. To achieve this, case log data is uploaded to the historical database by a surgical sales rep or case engineer using an online portal. In some embodiments, data transfer to the online database is wireless and automated.

Historical data sets from the online database are used as inputs to a machine learning model such as, for example, a recurrent neural network (RNN) or other form of artificial neural network. As is generally understood in the art, an artificial neural network functions similar to a biologic neural network and is comprised of a series of nodes and connections. The machine learning model is trained to predict one or more values based on the input data. For the sections that follow, it is assumed that the machine learning model is trained to generate predictor equations. These predictor equations may be optimized to determine the optimal size, position, and orientation of the implants to achieve the best outcome or satisfaction level.

Once the procedure is complete, all patient data and available outcome data, including the implant size, position and orientation determined by the CASS 100, are collected and stored in the historical database. Any subsequent calculation of the target equation via the RNN will include the data from the previous patient in this manner, allowing for continuous improvement of the system.

In addition to, or as an alternative to determining implant positioning, in some embodiments, the predictor equation and associated optimization can be used to generate the resection planes for use with a PSKI system. When used with a PSKI system, the predictor equation computation and optimization are completed prior to surgery. Patient anatomy is estimated using medical image data (x-ray, CT, MRI). Global optimization of the predictor equation can provide an ideal size and position of the implant components. Boolean intersection of the implant components and patient anatomy is defined as the resection volume. PSKI can be produced to remove the optimized resection envelope. In this embodiment, the surgeon cannot alter the surgical plan intraoperatively.

The surgeon may choose to alter the surgical case plan at any time prior to or during the procedure. If the surgeon elects to deviate from the surgical case plan, the altered size, position, and/or orientation of the component(s) is locked, and the global optimization is refreshed based on the new size, position, and/or orientation of the component(s) (using the techniques previously described) to find the new ideal position of the other component(s) and the corresponding resections needed to be performed to achieve the newly optimized size, position and/or orientation of the component(s). For example, if the surgeon determines that the size, position and/or orientation of the femoral implant in a TKA needs to be updated or modified intraoperatively, the femoral implant position is locked relative to the anatomy, and the new optimal position of the tibia will be calculated (via global optimization) considering the surgeon's changes to the femoral implant size, position and/or orientation. Furthermore, if the surgical system used to implement the case plan is robotically assisted (e.g., as with NAVIO® or the MAKO Rio), bone removal and bone morphology during the surgery can be monitored in real time. If the resections made during the procedure deviate from the surgical plan, the subsequent placement of additional components may be optimized by the processor taking into account the actual resections that have already been made.

Figure 7A:
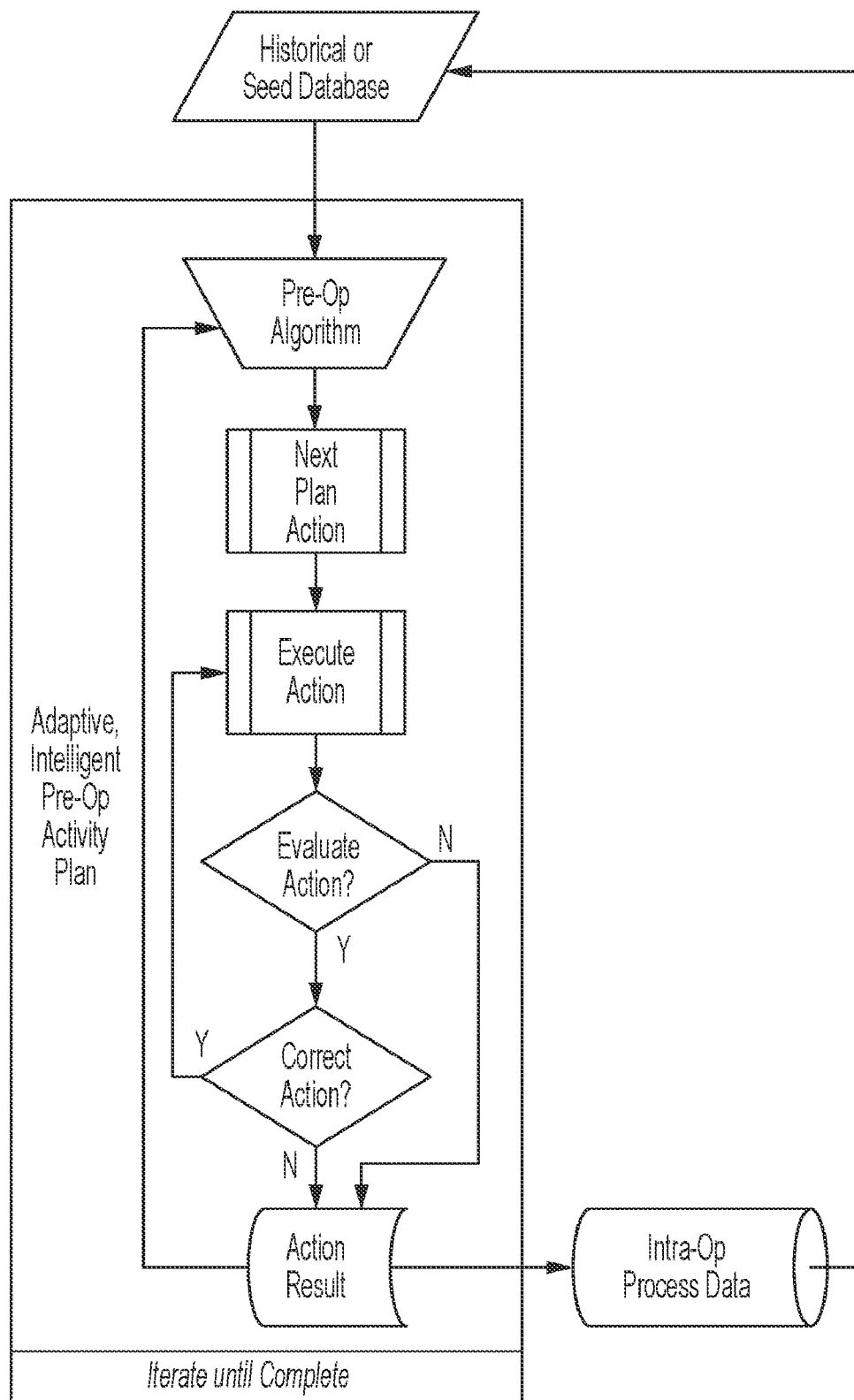
FIG. 7A depicts an illustrative flow diagram for determining a pre-operative surgical plan in accordance with an embodiment.
Figure 7B:
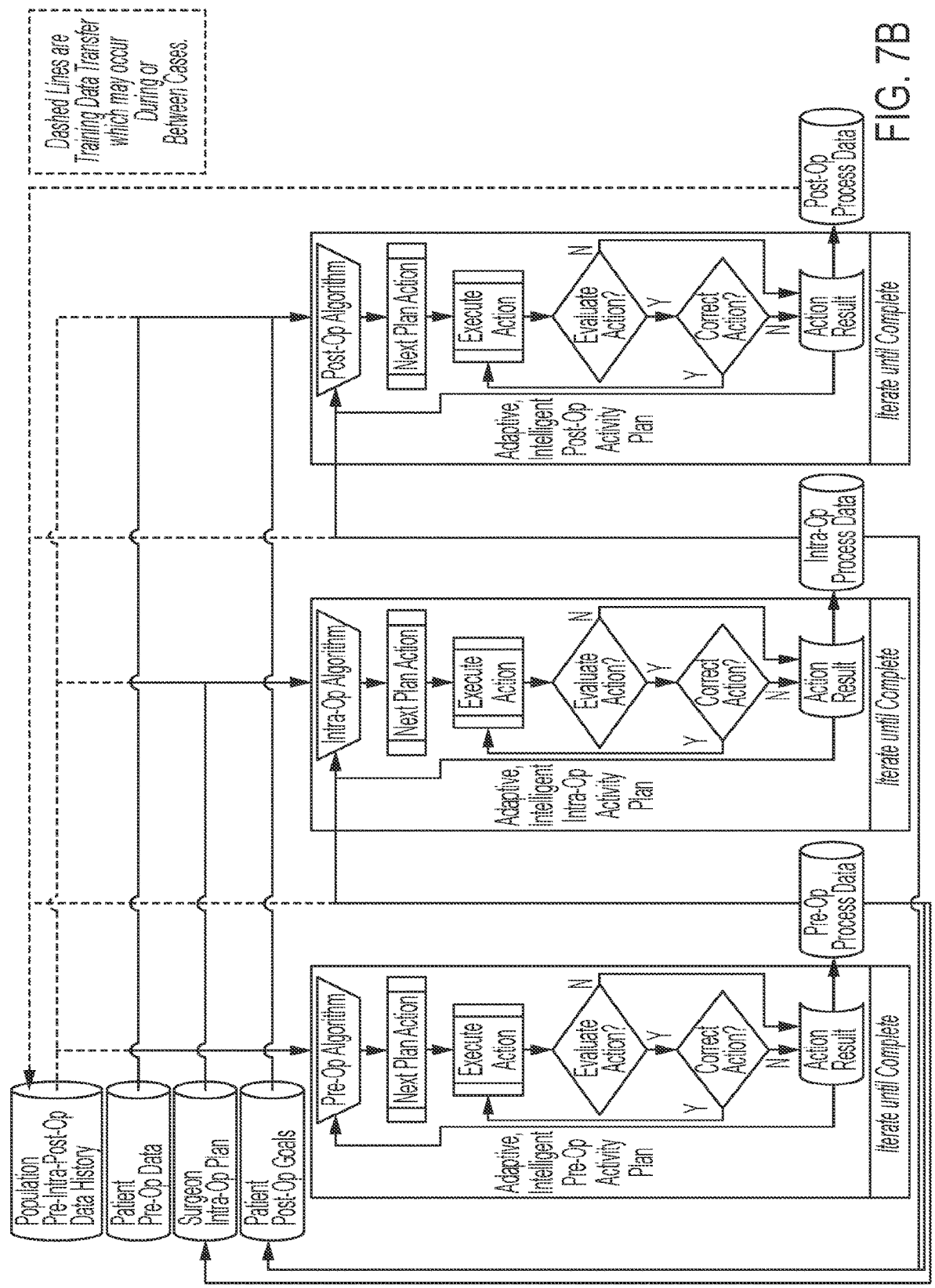
FIG. 7B depicts an illustrative flow diagram for determining an episode of care including pre-operative, intraoperative, and post-operative actions in accordance with an embodiment.

FIG. 7A illustrates how the Operative Patient Care System 620 may be adapted for performing case plan matching services. In this example, data is captured relating to the current patient 610 and is compared to all or portions of a historical database of patient data and associated outcomes 615. For example, the surgeon may elect to compare the plan for the current patient against a subset of the historical database. Data in the historical database can be filtered to include, for example, only data sets with favorable outcomes, data sets corresponding to historical surgeries of patients with profiles that are the same or similar to the current patient profile, data sets corresponding to a particular surgeon, data sets corresponding to a particular element of the surgical plan (e.g., only surgeries where a particular ligament is retained), or any other criteria selected by the surgeon or medical professional. If, for example, the current patient data matches or is correlated with that of a previous patient who experienced a good outcome, the case plan from the previous patient can be accessed and adapted or adopted for use with the current patient. The predictor equation may be used in conjunction with an intra-operative algorithm that identifies or determines the actions associated with the case plan. Based on the relevant and/or preselected information from the historical database, the intra-operative algorithm determines a series of recommended actions for the surgeon to perform. Each execution of the algorithm produces the next action in the case plan. If the surgeon performs the action, the results are evaluated. The results of the surgeon's performing the action are used to refine and update inputs to the intra-operative algorithm for generating the next step in the case plan. Once the case plan has been fully executed all data associated with the case plan, including any deviations performed from the recommended actions by the surgeon, are stored in the database of historical data. In some embodiments, the system utilizes preoperative, intraoperative, or postoperative modules in a piecewise fashion, as opposed to the entire continuum of care. In other words, caregivers can prescribe any permutation or combination of treatment modules including the use of a single module. These concepts are illustrated in FIG. 7B and can be applied to any type of surgery utilizing the CASS 100.

Surgery Process Display

As noted above with respect to FIGS. 1 and 5A-5C, the various components of the CASS 100 generate detailed data records during surgery. The CASS 100 can track and record various actions and activities of the surgeon during each step of the surgery and compare actual activity to the pre-operative or intraoperative surgical plan. In some embodiments, a software tool may be employed to process this data into a format where the surgery can be effectively "played-back." For example, in one embodiment, one or more GUIs may be used that depict all of the information presented on the Display 125 during surgery. This can be supplemented with graphs and images that depict the data collected by different tools. For example, a GUI that provides a visual depiction of the knee during tissue resection may provide the measured torque and displacement of the resection equipment adjacent to the visual depiction to better provide an understanding of any deviations that occurred from the planned resection area. The ability to review a playback of the surgical plan or toggle between different phases of the actual surgery vs. the surgical plan could provide benefits to the surgeon and/or surgical staff, allowing such persons to identify any deficiencies or challenging phases of a surgery so that they can be modified in future surgeries. Similarly, in academic settings, the aforementioned GUIs can be used as a teaching tool for training future surgeons and/or surgical staff. Additionally, because the data set effectively records many elements of the surgeon's activity, it may also be used for other reasons (e.g., legal or compliance reasons) as evidence of correct or incorrect performance of a particular surgical procedure.

Over time, as more and more surgical data is collected, a rich library of data may be acquired that describes surgical procedures performed for various types of anatomy (knee, shoulder, hip, etc.) by different surgeons for different patients. Moreover, information such as implant type and dimension, patient demographics, etc. can further be used to enhance the overall dataset. Once the dataset has been established, it may be used to train a machine learning model (e.g., RNN) to make predictions of how surgery will proceed based on the current state of the CASS 100.

Training of the machine learning model can be performed as follows. The overall state of the CASS 100 can be sampled over a plurality of time periods for the duration of the surgery. The machine learning model can then be trained to translate a current state at a first time period to a future state at a different time period. By analyzing the entire state of the CASS 100 rather than the individual data items, any causal effects of interactions between different components of the CASS 100 can be captured. In some embodiments, a plurality of machine learning models may be used rather than a single model. In some embodiments, the machine learning model may be trained not only with the state of the CASS 100, but also with patient data (e.g., captured from an EMR) and an identification of members of the surgical staff. This allows the model to make predictions with even greater specificity. Moreover, it allows surgeons to selectively make predictions based only on their own surgical experiences if desired.

Figure 7C:
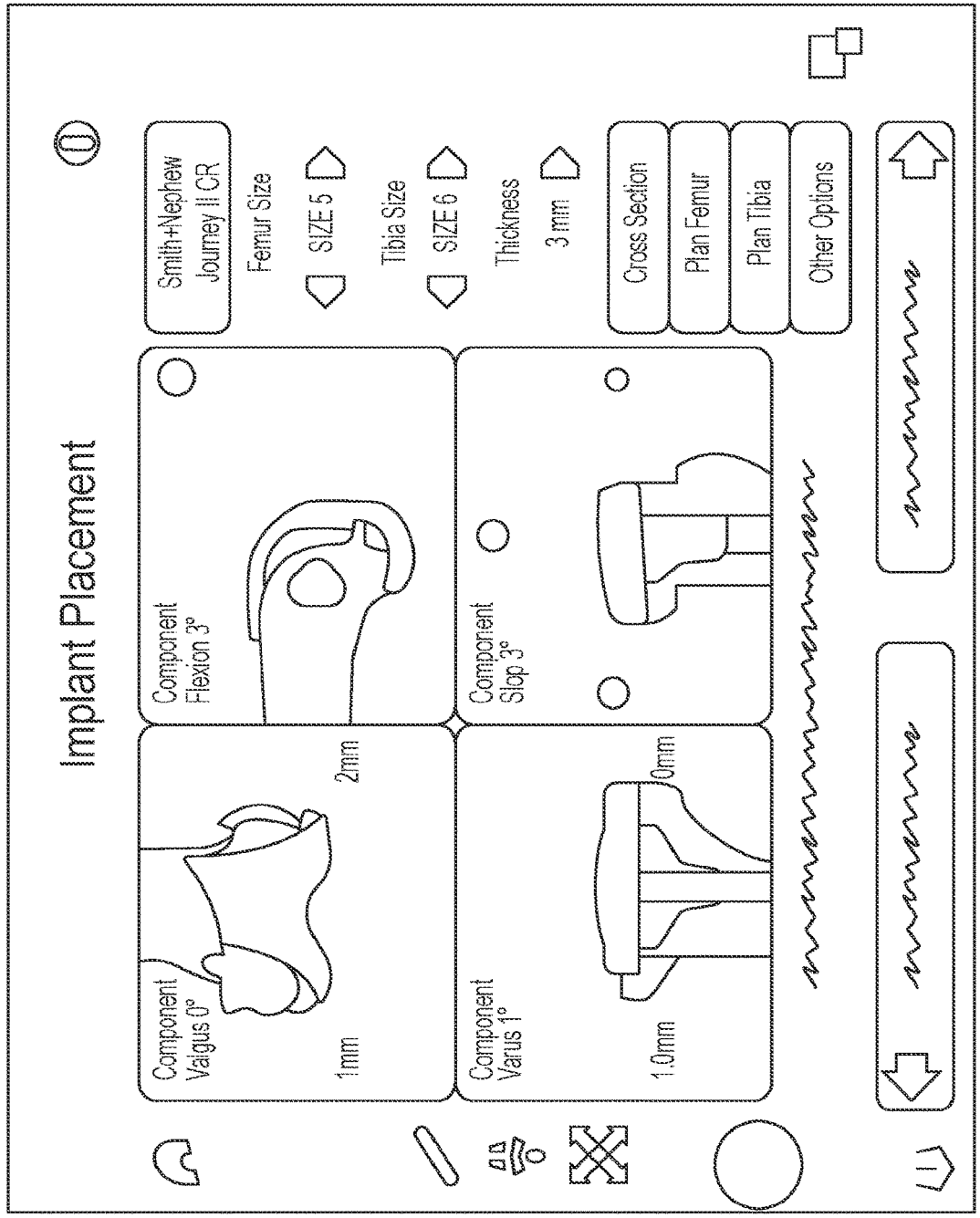
FIG. 7C depicts illustrative graphical user interfaces including images depicting an implant placement in accordance with an embodiment.
Figure 7C:
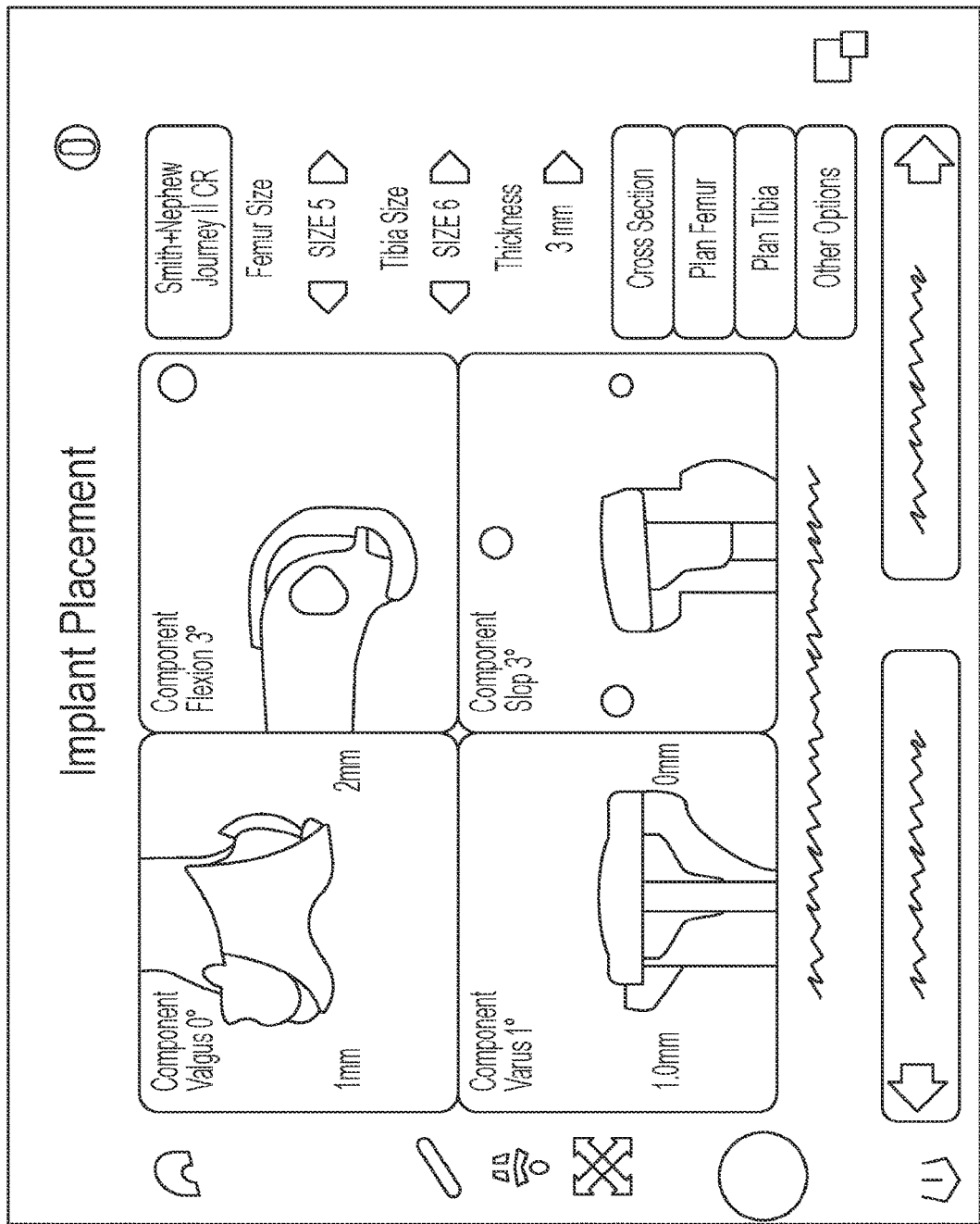
Figure 7C:
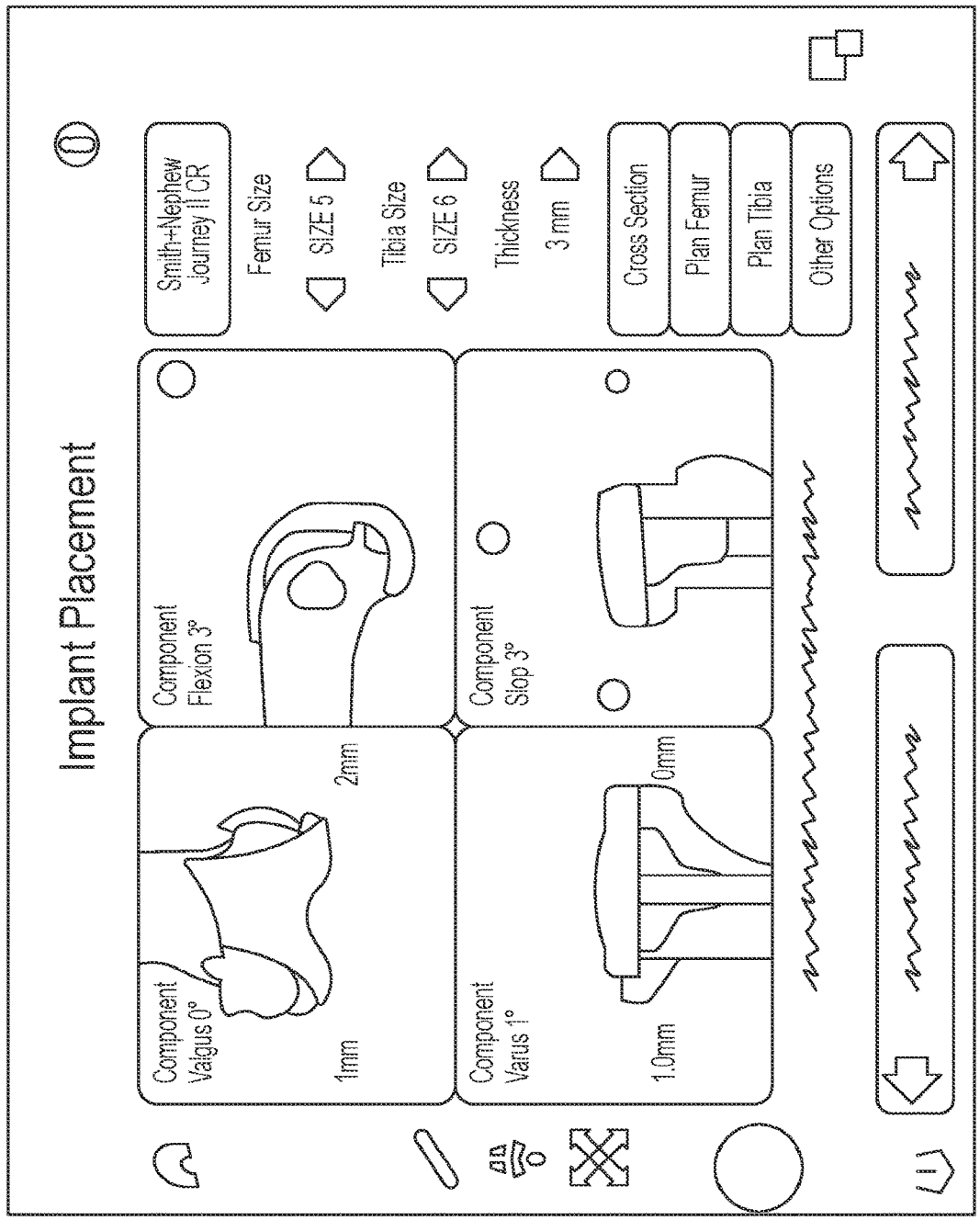

In some embodiments, predictions or recommendations made by the aforementioned machine learning models can be directly integrated into the surgical workflow. For example, in some embodiments, the Surgical Computer 150 may execute the machine learning model in the background making predictions or recommendations for upcoming actions or surgical conditions. A plurality of states can thus be predicted or recommended for each period. For example, the Surgical Computer 150 may predict or recommend the state for the next 5 minutes in 30 second increments. Using this information, the surgeon can utilize a "process display" view of the surgery that allows visualization of the future state. For example, FIG. 7C depicts a series of images that may be displayed to the surgeon depicting the implant placement interface. The surgeon can cycle through these images, for example, by entering a particular time into the display 125 of the CASS 100 or instructing the system to advance or rewind the display in a specific time increment using a tactile, oral, or other instruction. In one embodiment, the process display can be presented in the upper portion of the surgeon's field of view in the AR HMD. In some embodiments, the process display can be updated in real-time. For example, as the surgeon moves resection tools around the planned resection area, the process display can be updated so that the surgeon can see how his or her actions are affecting the other factors of the surgery.

In some embodiments, rather than simply using the current state of the CASS 100 as an input to the machine learning model, the inputs to the model may include a planned future state. For example, the surgeon may indicate that he or she is planning to make a particular bone resection of the knee joint. This indication may be entered manually into the Surgical Computer 150 or the surgeon may verbally provide the indication. The Surgical Computer 150 can then produce a film strip showing the predicted effect of the cut on the surgery. Such a film strip can depict over specific time increments how the surgery will be affected, including, for example, changes in the patient's anatomy, changes to implant position and orientation, and changes regarding surgical intervention and instrumentation, if the contemplated course of action were to be performed. A surgeon or medical professional can invoke or request this type of film strip at any point in the surgery to preview how a contemplated course of action would affect the surgical plan if the contemplated action were to be carried out.

It should be further noted that, with a sufficiently trained machine learning model and robotic CASS, various elements of the surgery can be automated such that the surgeon only needs to be minimally involved, for example, by only providing approval for various steps of the surgery. For example, robotic control using arms or other means can be gradually integrated into the surgical workflow over time with the surgeon slowly becoming less and less involved with manual interaction versus robot operation. The machine learning model in this case can learn what robotic commands are required to achieve certain states of the CASS-implemented plan. Eventually, the machine learning model may be used to produce a film strip or similar view or display that predicts and can preview the entire surgery from an initial state. For example, an initial state may be defined that includes the patient information, the surgical plan, implant characteristics, and surgeon preferences. Based on this information, the surgeon could preview an entire surgery to confirm that the CASS-recommended plan meets the surgeon's expectations and/or requirements. Moreover, because the output of the machine learning model is the state of the CASS 100 itself, commands can be derived to control the components of the CASS to achieve each predicted state. In the extreme case, the entire surgery could thus be automated based on just the initial state information.

Using the Point Probe to Acquire High-Resolution of Key Areas During Hip Surgeries Use of the point probe is described in U.S. patent application Ser. No. 14/955,742 entitled "Systems and Methods for Planning and Performing Image Free Implant Revision Surgery," the entirety of which is incorporated herein by reference. Briefly, an optically tracked point probe may be used to map the actual surface of the target bone that needs a new implant. Mapping is performed after removal of the defective or worn-out implant, as well as after removal of any diseased or otherwise unwanted bone. A plurality of points is collected on the bone surfaces by brushing or scraping the entirety of the remaining bone with the tip of the point probe. This is referred to as tracing or "painting" the bone. The collected points are used to create a three-dimensional model or surface map of the bone surfaces in the computerized planning system. The created 3D model of the remaining bone is then used as the basis for planning the procedure and necessary implant sizes. An alternative technique that uses X-rays to determine a 3D model is described in U.S. patent application Ser. No. 16/387, 151, filed Apr. 17, 2019 and entitled "Three-Dimensional Selective Bone Matching" and U.S. patent application Ser. No. 16/789,930, filed Feb. 13, 2020 and entitled "Three-Dimensional Selective Bone Matching," the entirety of each of which is incorporated herein by reference.

For hip applications, the point probe painting can be used to acquire high resolution data in key areas such as the acctabular rim and acetabular fossa. This can allow a surgeon to obtain a detailed view before beginning to ream. For example, in one embodiment, the point probe may be used to identify the floor (fossa) of the acetabulum. As is well understood in the art, in hip surgeries, it is important to ensure that the floor of the acetabulum is not compromised during reaming so as to avoid destruction of the medial wall. If the medial wall were inadvertently destroyed, the surgery would require the additional step of bone grafting. With this in mind, the information from the point probe can be used to provide operating guidelines to the acetabular reamer during surgical procedures. For example, the acetabular reamer may be configured to provide haptic feedback to the surgeon when he or she reaches the floor or otherwise deviates from the surgical plan. Alternatively, the CASS 100 may automatically stop the reamer when the floor is reached or when the reamer is within a threshold distance.

As an additional safeguard, the thickness of the area between the acetabulum and the medial wall could be estimated. For example, once the acetabular rim and acetabular fossa has been painted and registered to the pre-operative 3D model, the thickness can readily be estimated by comparing the location of the surface of the acetabulum to the location of the medial wall. Using this knowledge, the CASS 100 may provide alerts or other responses in the event that any surgical activity is predicted to protrude through the acetabular wall while reaming.

The point probe may also be used to collect high resolution data of common reference points used in orienting the 3D model to the patient. For example, for pelvic plane landmarks like the ASIS and the pubic symphysis, the surgeon may use the point probe to paint the bone to represent a true pelvic plane. Given a more complete view of these landmarks, the registration software has more information to orient the 3D model.

The point probe may also be used to collect high-resolution data describing the proximal femoral reference point that could be used to increase the accuracy of implant placement. For example, the relationship between the tip of the Greater Trochanter (GT) and the center of the femoral head is commonly used as reference point to align the femoral component during hip arthroplasty. The alignment is highly dependent on proper location of the GT; thus, in some embodiments, the point probe is used to paint the GT to provide a high-resolution view of the area. Similarly, in some embodiments, it may be useful to have a high-resolution view of the Lesser Trochanter (LT). For example, during hip arthroplasty, the Dorr Classification helps to select a stem that will maximize the ability of achieving a press-fit during surgery to prevent micromotion of femoral components post-surgery and ensure optimal bony ingrowth. As is generated understood in the art, the Dorr Classification measures the ratio between the canal width at the LT and the canal width 10 cm below the LT. The accuracy of the classification is highly dependent on the correct location of the relevant anatomy. Thus, it may be advantageous to paint the LT to provide a high-resolution view of the area.

In some embodiments, the point probe is used to paint the femoral neck to provide high-resolution data that allows the surgeon to better understand where to make the neck cut. The navigation system can then guide the surgeon as they perform the neck cut. For example, as understood in the art, the femoral neck angle is measured by placing one line down the center of the femoral shaft and a second line down the center of the femoral neck. Thus, a high-resolution view of the femoral neck (and possibly the femoral shaft as well) would provide a more accurate calculation of the femoral neck angle.

High-resolution femoral head neck data also could be used for a navigated resurfacing procedure where the software/hardware aids the surgeon in preparing the proximal femur and placing the femoral component. As is generally understood in the art, during hip resurfacing, the femoral head and neck are not removed; rather, the head is trimmed and capped with a smooth metal covering. In this case, it would be advantageous for the surgeon to paint the femoral head and cap so that an accurate assessment of their respective geometries can be understood and used to guide trimming and placement of the femoral component.

Registration of Pre-Operative Data to Patient Anatomy Using the Point Probe

As noted above, in some embodiments, a 3D model is developed during the pre-operative stage based on 2D or 3D images of the anatomical area of interest. In such embodiments, registration between the 3D model and the surgical site is performed prior to the surgical procedure. The registered 3D model may be used to track and measure the patient's anatomy and surgical tools intraoperatively.

During the surgical procedure, landmarks are acquired to facilitate registration of this pre-operative 3D model to the patient's anatomy. For knee procedures, these points could comprise the femoral head center, distal femoral axis point, medial and lateral epicondyles, medial and lateral malleolus, proximal tibial mechanical axis point, and tibial A/P direction. For hip procedures these points could comprise the anterior superior iliac spine (ASIS), the pubic symphysis, points along the acetabular rim and within the hemisphere, the greater trochanter (GT), and the lesser trochanter (LT).

In a revision surgery, the surgeon may paint certain areas that contain anatomical defects to allow for better visualization and navigation of implant insertion. These defects can be identified based on analysis of the pre-operative images. For example, in one embodiment, each pre-operative image is compared to a library of images showing "healthy" anatomy (i.e., without defects). Any significant deviations between the patient's images and the healthy images can be flagged as a potential defect. Then, during surgery, the surgeon can be warned of the possible defect via a visual alert on the display 125 of the CASS 100. The surgeon can then paint the area to provide further detail regarding the potential defect to the Surgical Computer 150.

In some embodiments, the surgeon may use a non-contact method for registration of bony anatomy intra-incision. For example, in one embodiment, laser scanning is employed for registration. A laser stripe is projected over the anatomical area of interest and the height variations of the area are detected as changes in the line. Other non-contact optical methods, such as white light interferometry or ultrasound, may alternatively be used for surface height measurement or to register the anatomy. For example, ultrasound technology may be beneficial where there is soft tissue between the registration point and the bone being registered (e.g., ASIS, pubic symphysis in hip surgeries), thereby providing for a more accurate definition of anatomic planes.

Fiber Optic Shape Sensing (FOSS) Devices and Surgical Tracking Systems

Referring to FIG. 8, FOSS device configurations 800A-C that can be used to facilitate improved tracking of patient anatomy and/or instruments in surgical environments are illustrated. The FOSS device configurations 800A-C according to some examples of this technology are configured to use light along an optical fiber to reconstruct the shape along that fiber. The FOSS device configurations 800A-C use distributed strain measurement in the optical fiber using characteristic Rayleigh backscatter or controlled grating patterns, for example. The shape along the optical fiber begins at a specific point along the sensor, referred to herein as the launch or z=0, and the subsequent shape position and orientation are relative to that point.

FOSS device configurations 800A-C that can be used with one or more of the examples described and illustrated herein include single point sensors (e.g., FOSS device configuration 800A), quasi-distributed sensors (also referred to as Fiber Bragg Grating (FBG) sensors) (e.g., FOSS device configuration 800B), and distributed sensors (FOSS device configuration 800C). Single point strain sensing is effective for bend measurement in one plane and shape sensing deployments requiring only one degree-of-freedom (DoF). FBGs are interference filters inscribed into the core of an optical fiber, which reflect a specific wavelength. Combining multiple FBGs at the same longitudinal position allows the curvature and direction angle to be calculated. Multiplexing interrogation techniques also allows reading of multiple FBG sensors to measure a combination of parameters using a single fiber.

FBGs are made in some examples by lateral exposure of an optical fiber with a periodic pattern of laser light. The generated pattern is translated into a permanent refractive index change inside the fiber core forming a grating. The resulting FBG acts as a wavelength selective mirror for one distinct wavelength (i.e.., the Bragg wavelength). When an optical fiber having several FBGs is exposed to broadband light, each grating reflects a certain amount of the light at a different Bragg wavelength, which is spectrally detected. Various optical fiber arrangements, such as multiple fibers, a multicore fiber, and an embedded fiber in an object can be used in one or more of the examples of this technology, as described and illustrated herein. In some examples, there are a number of multi-directional joints or continuous flexible objects that provide for a more distributed sensing technology.

Referring to FIGS. 9A-B, the FOSS device 900 facilitates shape sensing in three dimensions using three single mode cores with strain sensors 902A-C creating a tri-core directional bend sensing system, although more than three single mode cores can also be used in other examples. With three single mode cores, it is an indication of an upward bend when the top sensor 902A is stretched and the bottom two sensors 902B-C are compressed, as illustrated in FIG. 9B.

Accordingly, bending of the optical fiber induces strain on the cores that can be measured by monitoring the wavelength shifts in each core. By having two or more cores disposed off-axis in the optical fiber, bending of the optical fiber induces different strains on each of the cores. These strains are a function of the local bend radius of the optical fiber, the radial position of the core with respect to the optical fiber centerline, and the angular position of the core.

Figure 10:
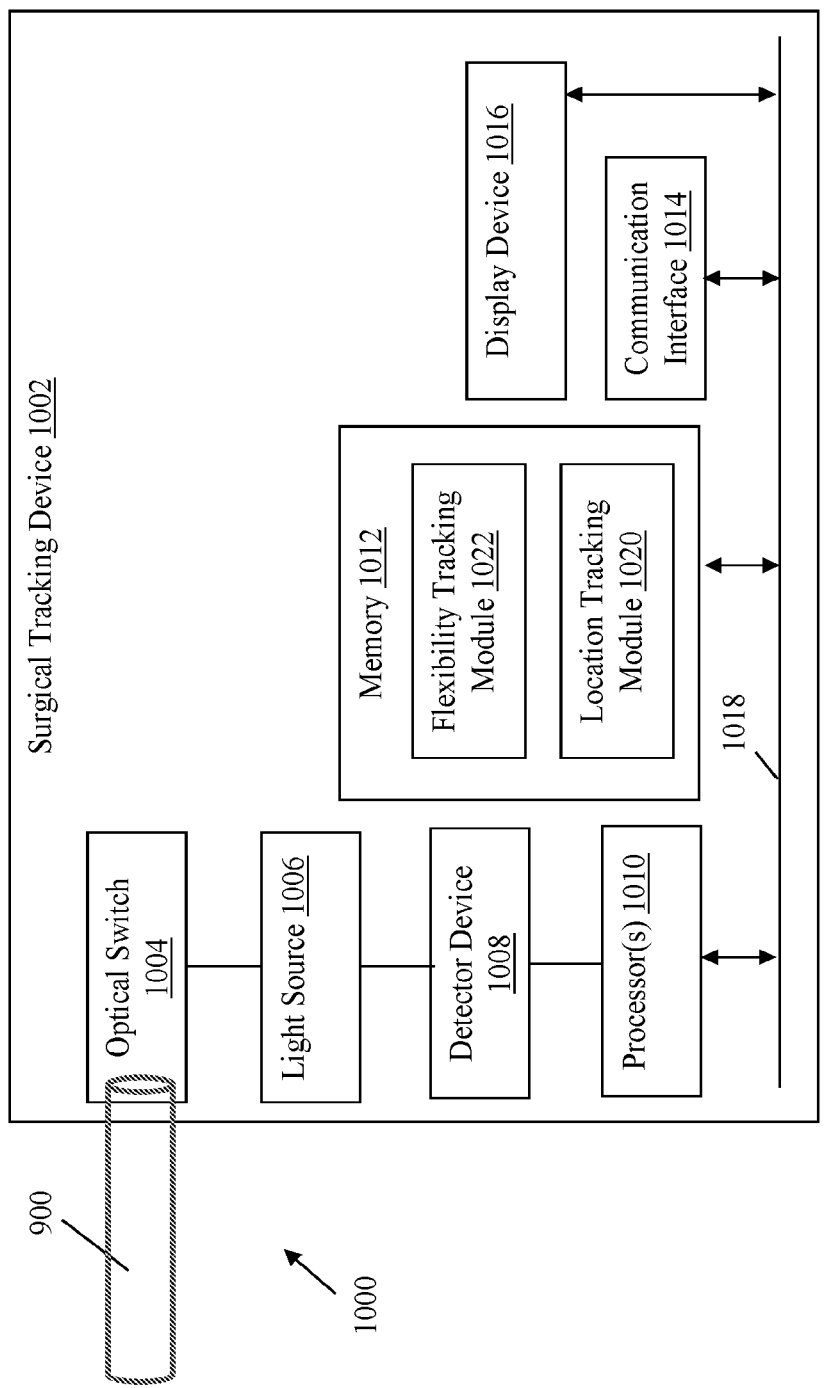
FIG. 10 depicts a block diagram of an exemplary tracking system that can be used to facilitate improved tracking of patient anatomy and/or instruments in surgical environments in accordance with an embodiment.

Referring to FIG. 10, a block diagram of a tracking system 1000 that can be used to facilitate improved tracking of patient anatomy and/or instruments in surgical environments is illustrated. The system 1000 in this example includes at least one FOSS device 900 coupled to a surgical tracking device 1002 via an optical switch 1004 of the surgical tracking device. The surgical tracking device 1002 further includes a light source 1006 coupled to the optical switch 1004 and a detector device 1008. The detector device 1008 is coupled to processor(s) 1010 of the surgical tracking device 1002, which further includes memory 1012, a communication interface 1014, and a display device 1016 coupled to the processor(s) 1010 via a bus 1018 or other communication link, although the surgical tracking device can include other types, or another number, of elements in other configurations in other examples.

The light source 1006 in this example can be a tunable laser or broadband light source configured to emit light through the optical switch 1004 and FOSS device 900. The optical switch 1004 is optionally configured to sequentially switch between a multiplex of individual fibers inside the FOSS device 900 for signal detection by the detector device 1008. In particular, the detector device 1008 can measure and digitize the real-time reflectivity at one or more wavelengths of the strain sensors 902A-C at one or more locations of the FOSS device 900, which is obtained by the processor(s) 1010. The digital reflectivity data can facilitate construction of a three-dimensional shape of the optical fiber of the FOSS device 900, as described and illustrated in more detail by way of the examples herein.

The processor(s) 1010 of the surgical tracking device 1002 may execute programmed instructions stored in the memory 1012 of the surgical tracking device for any number of the functions described and illustrated herein. The processor(s) 1010 may include, for example, one or more central processing units (CPUs), one or more processing cores, configurable hardware logic (e.g., ASIC(s) and/or FPGA(s)), or a combination thereof, although other types of processor(s) and/or component(s) can also be used.

The memory 1012 of the surgical tracking device 1002 stores these programmed instructions for one or more aspects of the present technology as described and illustrated herein, although some or all of the programmed instructions could be stored elsewhere. A variety of different types of memory storage devices, such as RAM, ROM, hard disk, SSDs, flash memory, and/or other computer readable media that are read from and written to by a magnetic, optical, or other reading and writing system that is coupled to the processor(s) 1010, can be used for the memory 1012.

Accordingly, the memory 1012 of the surgical tracking device 1002 can store one or more modules that can include computer executable instructions that, when executed by the surgical tracking device, cause the surgical tracking device to perform actions, such as to transmit, receive, or otherwise process communications, for example, and to perform other actions described and illustrated herein, for example. The modules can be implemented as components of other modules. Further, the modules can be implemented as applications, operating system extensions, plugins, or the like.

In this particular example, the memory 1012 of the surgical tracking device 1002 includes a location tracking module 1020 and a flexibility tracking module 1022. The location tracking module 1020 is configured to interpret the digitized reflectivity data provided via the processor(s) 1010 from the detector device 1008, as well as model(s) based on preoperative or intraoperative imaging of patient anatomy, for example, and register location(s) of portion(s) of the optical fiber of the FOSS device 900 within the coordinate system of the model(s).

Accordingly, the location tracking module 1020 is configured to interpret output from the FOSS device 900 to determine the location of tracked anatomy or instrument(s) to which the FOSS device is attached. Optionally, the location tracking module 1020 can be configured to output tracking data to facilitate automated control (e.g., by surgical computer 150) of a location and/or operation of a tracked instrument, for example. The operation of the location tracking module 1020 is described and illustrated in more detail below with reference to FIGS. 11-15.

The flexibility tracking module 1022 is configured to interpret the digitized reflectivity data provided via the processor(s) 1010 from the detector device 1008 and determine the location and extent of flexion at portion(s) of the optical fiber of the FOSS device 900. Optionally, the location of the portion(s) can be determined based on a registration as explained above, although other methods of determining the location can also be used. The extent of the flexion can be determined based on the reflectivity of the output of the light source 1006 in relation to the sensors 902A-C, for example.

Accordingly, the flexibility tracking module 1022 is configured to interpret output from the FOSS device 900 to determine the flexion of tracked instrument(s) to which the FOSS device is attached. Optionally, the flexibility tracking module 1022 can be configured to output flexibility data to facilitate automated control (e.g., by surgical computer 150) of a location and/or operation of a tracked instrument, for example. The operation of the flexibility tracking module 1022 is described and illustrated in more detail below with reference to FIG. 16.

Referring back to FIG. 10, the communication interface 1014 of the surgical tracking device 1002 operatively couples and communicates between the surgical tracking device and the surgical computer 150 of the CASS system 100. In these examples, the surgical tracking device 1002 and the surgical computer 150 can be coupled together by a direct, wired connection or communication network(s), for example, although other types of connections or configurations can also be used. By way of example only, the connection(s) and/or communication network(s) can include local area network(s) (LAN(s)) that use TCP/IP over Ethernet and industry-standard protocols or Bluetooth™ or other short range protocols, for example, although other types or numbers of protocols or communication networks can be used.

The display device 1016 of the surgical tracking device 1002 can include any type of monitor or screen configured to provide a visual image. Optionally, the surgical tracking device 1002 can further include an input device (not shown) such as a keyboard or mouse, or any other type of device configured to enable a human operator to interact with the surgical tracking device, such as to input and/or view selection, configurations, and other data, for example. In yet other examples, the display device 1016 and the input device are integrated into a single device, such as in the form of a capacitive touchscreen, for example, and other types, or another number, of input and/or display devices could also be used in other examples.

While the surgical tracking device 1002 is illustrated in this example as including a single device, the surgical tracking device in other examples can include a plurality of devices each having one or more processors (each processor with one or more processing cores) that implement one or more steps of this technology. In these examples, one or more of the devices can have a dedicated communication interface or memory. Alternatively, one or more of the devices can utilize the memory, communication interface, or other hardware or software components of one or more other devices included in the surgical tracking device 1002. Additionally, one or more of the devices that together comprise the surgical tracking device 1002 in other examples can be standalone devices or integrated with one or more other devices or apparatuses, such as the optical switch 1004, light source 1006, and/or detector device 1008, for example. Additionally, there may be more surgical tracking devices than are illustrated in the tracking system 1000 of FIG. 10.

In addition, a plurality of computing systems or devices can be substituted for any one of the systems or devices in any example. Accordingly, principles and advantages of distributed processing, such as redundancy and replication also can be implemented, as desired, to increase the robustness and performance of the devices and systems of the examples. Further, the surgical tracking device 1002 can be integrated with, or communicably coupled to, the surgical computer 150 of the CASS system 100 in some examples.

One or more of the examples described and illustrated herein also may be embodied as one or more non-transitory computer or machine readable media having instructions stored thereon, such as in the memory 1012 of the surgical tracking device 1002, for one or more aspects of the present technology. The instructions in some examples include executable code that, when executed by one or more processors, such as the processor(s) 1010 of the surgical tracking device 1002, cause the processors to carry out step(s) necessary to implement the method(s) of the example(s) of this technology that will now be described and illustrated in more detail with reference to FIGS. 11-16.

Patient Anatomy Location Tracking

Figure 11:
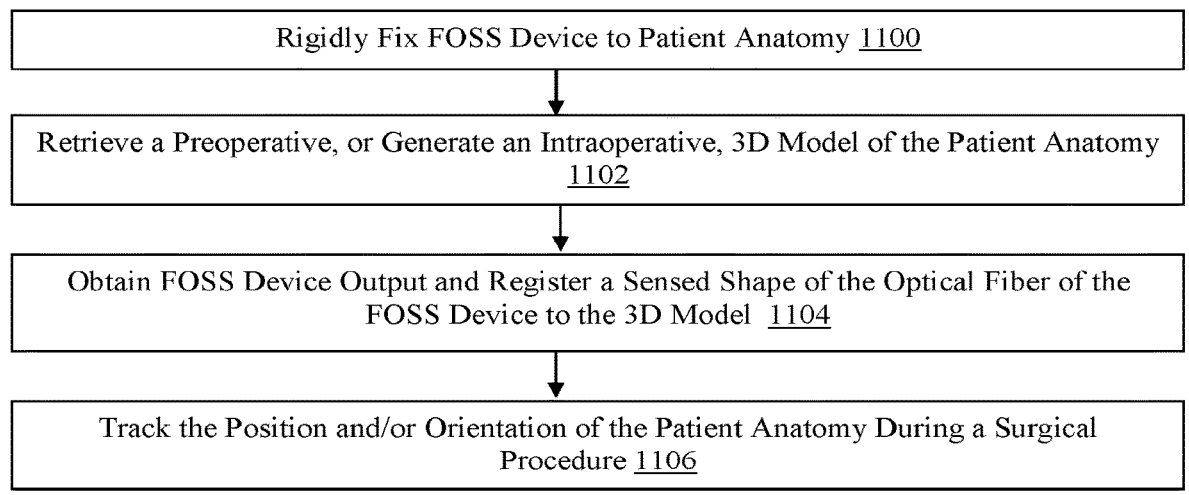
FIG. 11 depicts a flowchart of an exemplary method for tracking patient anatomy location using an exemplary FOSS device in accordance with an embodiment.

Referring more specifically to FIG. 11, a flowchart of an exemplary method for tracking patient anatomy location using the FOSS device 900 is illustrated. In this example, the tracking system 1000 is used to track patient anatomy based on a location/orientation of a length, and/or a distal tip or other portion, of an optical fiber of the FOSS device 900, such as during an orthopedic and/or sports medicine surgical procedure, for example. In step 1100, the FOSS device 900 is rigidly attached to patient anatomy, with a non-anchored end of the FOSS device 900 optionally attached to a tracking tool. The FOSS device 900 can be pinned, clamped, attached using an adhesive, or inserted into the bone, for example, although other attachment methods can also be used. In other examples, the FOSS device 900 can be attached to a fixed object within an environment, such as an operating room table, for example, that is otherwise linked to, or has a known correspondence with, the patient anatomy.

Since the FOSS device 900 of this technology has relatively small size and weight, attachment to the targeted bone could be achieved less invasively than devices used for conventional tracking methods, which could be favorable to the patient, improve patient recovery, reduce complications, such as fractures and infection, and improve adoption. In one particular example, the FOSS device 900 can be placed through an arthroscopic portal that is already being used due to its relatively small size and flexibility.

In step 1102, the surgical tracking device 1002 retrieves a preoperative, or generates an intraoperative, three dimensional (3D) model of the patient anatomy to which the FOSS device 900 was rigidly attached in step 1100. The 3D model can be generated from a set of x-ray, MRI, or CT images, for example, although any other method of generating the 3D model can also be used. In other examples, other types of models and/or two dimensional (2D) images can also be obtained in step 1102.

In step 1104, the surgical tracking device 1002 obtains output (e.g., digital reflectivity data) from the FOSS device 900, and/or a probe attached to an end of the optical fiber of the FOSS device 900, and outputs a sensed shape of the optical fiber of the FOSS device 900, which is determined from the output, to the 3D model retrieved or generated in step 1102. In particular, the light source 1006 emits light and the optical switch 1004 and detector device 1008 facilitate receiving and digitizing optical reflection from the sensors 902A-C in each of the cores of the optical fiber of the FOSS device 900. Accordingly, in this example, the tracking system 1000 facilitates rapid registration of bony anatomy of a joint, for example, when the anatomy is known based on preoperative or intraoperative imaging, for example.

Figure 12:
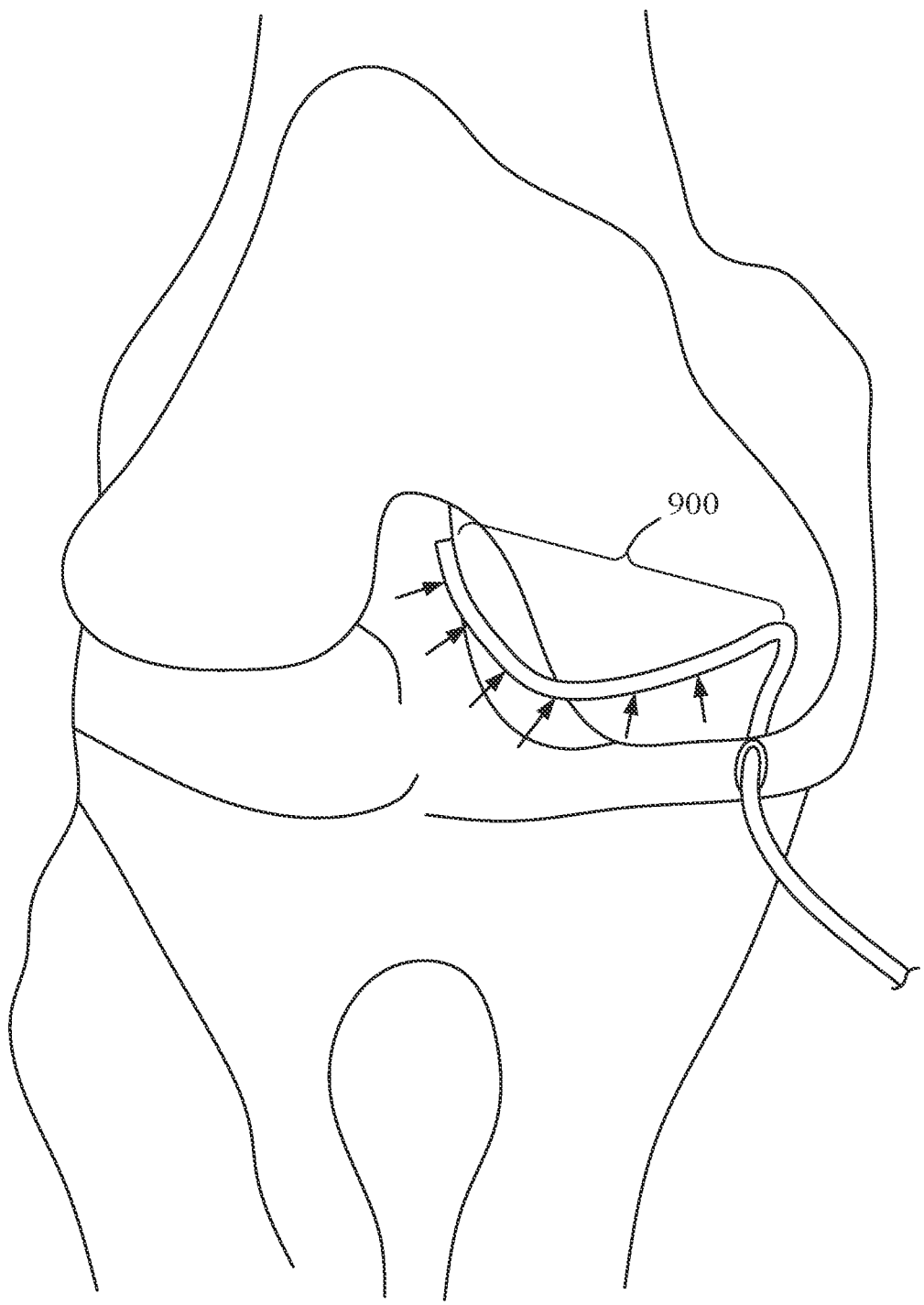
FIG. 12 depicts an exemplary FOSS device for facilitating rapid registration in accordance with an embodiment.

Referring to FIG. 12, an exemplary deployment of the FOSS device 900 for facilitating rapid registration is illustrated. In this example, the FOSS device 900 is placed directly on, wrapped around, or otherwise biased against, the bone of a patient to facilitate collection of a plurality of points along the surface of the bone. These points could be used to register the anatomy to a 3D model of the bone immediately without the need to collect many points by touching the surface of the bone or painting the surface of the bone with a separate tracked device, for example. These points may also be used to generate an accurate model of the 3D surface intraoperatively by placing the FOSS device 900 on the bone and dragging it along the surface.

Referring back to FIG. 11, in step 1106, the surgical tracking device 1002 tracks the position and/or orientation (i.e.., pose) of the patient anatomy during a surgical procedure. Accordingly, the surgical tracking device 1002 continuously obtains the output from the FOSS device 900 and, based on the registration in step 1104, tracks the position and/or orientation of the patient anatomy and optionally adjusts a display of the 3D model, or a portion thereof, output on the display device 1016 based on the tracking.

In one particular example of a total knee replacement or arthroscopic knee surgical procedure, the femur and tibia are each sensed with a FOSS device 900 attached to the bone by fixing at least one point of the FOSS device to each bone or passing the fiber through the bone. The optical reflection or scatter returns to the surgical tracking device 1002, which generates and outputs to the display device 1016, for example, the position of each bone. Accordingly, a single FOSS device 900 in this example is configured to track multiple anatomical structures, as described and illustrated in more detail below with reference to FIG. 15. In another example, multiple FOSS devices 900, such as FOSS devices separately attached to each of the femur and the tibia, can be co-registered to each other at the onset of a surgical procedure and used to intraoperatively track the anatomical structures.

Figure 13:
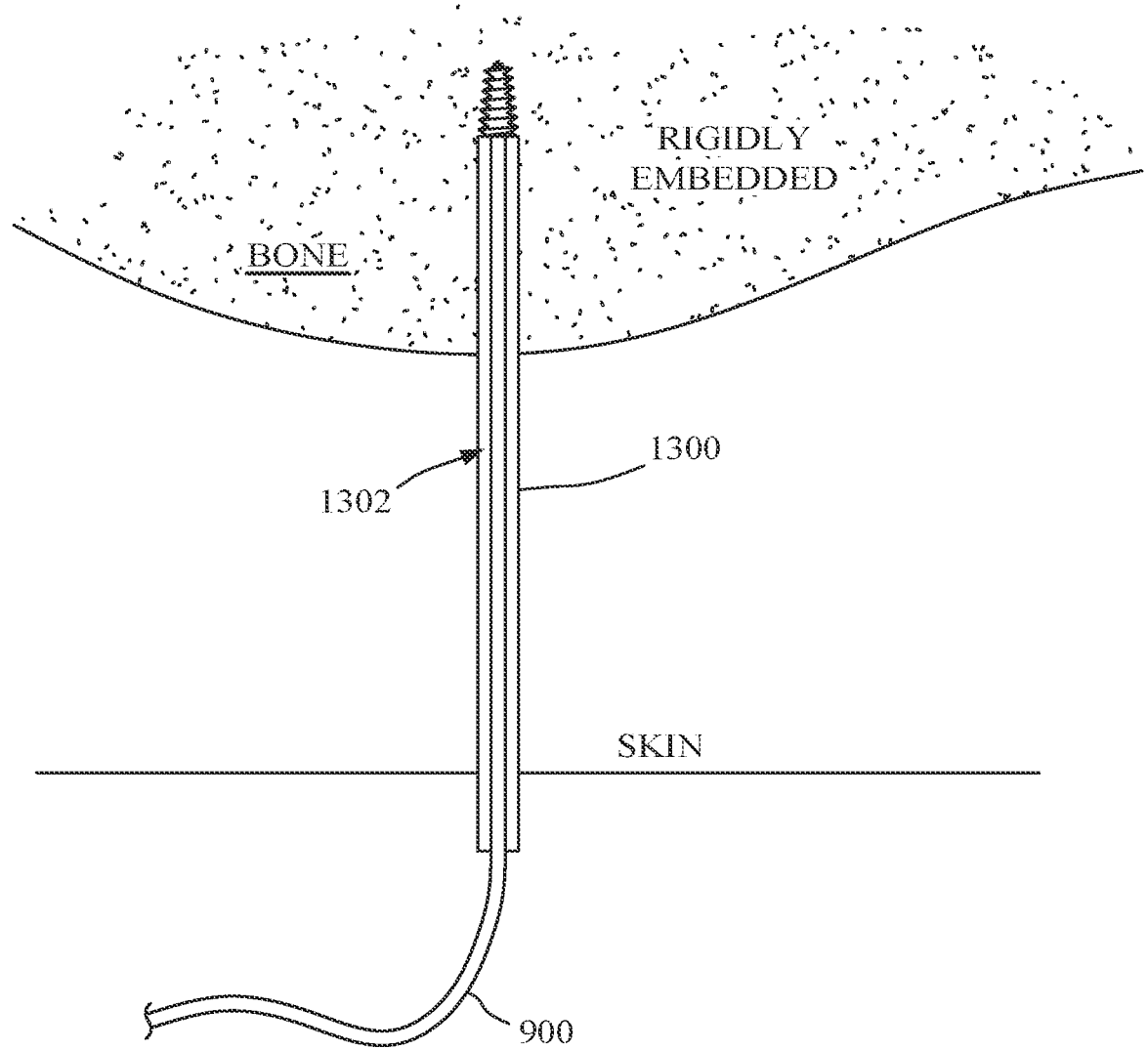
FIG. 13 depicts an exemplary FOSS device to facilitate tracking anatomy in a minimally invasive manner in accordance with an embodiment.

Referring to FIG. 13, an exemplary deployment of a FOSS device 900 to facilitate tracking anatomy in a minimally invasive manner is illustrated. In this example, a hollow needle 1300 having an inner lumen 1302 is percutaneously driven into bone. A portion of the FOSS device 900 is seated down the inner lumen 1302 at, or below, bone level so as to rigidly move with the bone. Advantageously, the FOSS device 900 could be reused in this example.

In yet another example, the FOSS device 900 is located along the inner lumen 1302 of the hollow needle 1300, which in this example is positioned in soft tissue. For example, in hip arthroscopy, entry into the joint is performed with a needle positioned in soft tissue with x-ray imaging. With this technology, the radiation associated with the x-ray imaging could advantageously be eliminated by tracking the hollow needle 1300 based on the tracked location of the FOSS device 900 while maintaining the existing surgical workflow of switching out the needle with a guidewire.

Although examples have been disclosed herein in which the FOSS device 900 is used to track rigid objects such as bone, it could also be used to track soft tissue deformity, such as the meniscus when attached, for example, around the meniscal rim. The FOSS device 900 in this example could track how the meniscus deforms throughout a range of motion or determine if the meniscus extrudes under load. In yet another example of an ACL reconstruction, the FOSS device 900 can be rigidly attached to potential tunnel/fixation points in the femur and tibia prior to drilling the tunnels. In this example, a user could determine whether there was any impingement during a range of motion or whether a planned graft length was adequate during flexion/extension, for example. Other deployments of the FOSS device 900 to track rigid objects and/or soft tissue can also be used in other examples.

Surgical Instrument Location Tracking

Figure 14:
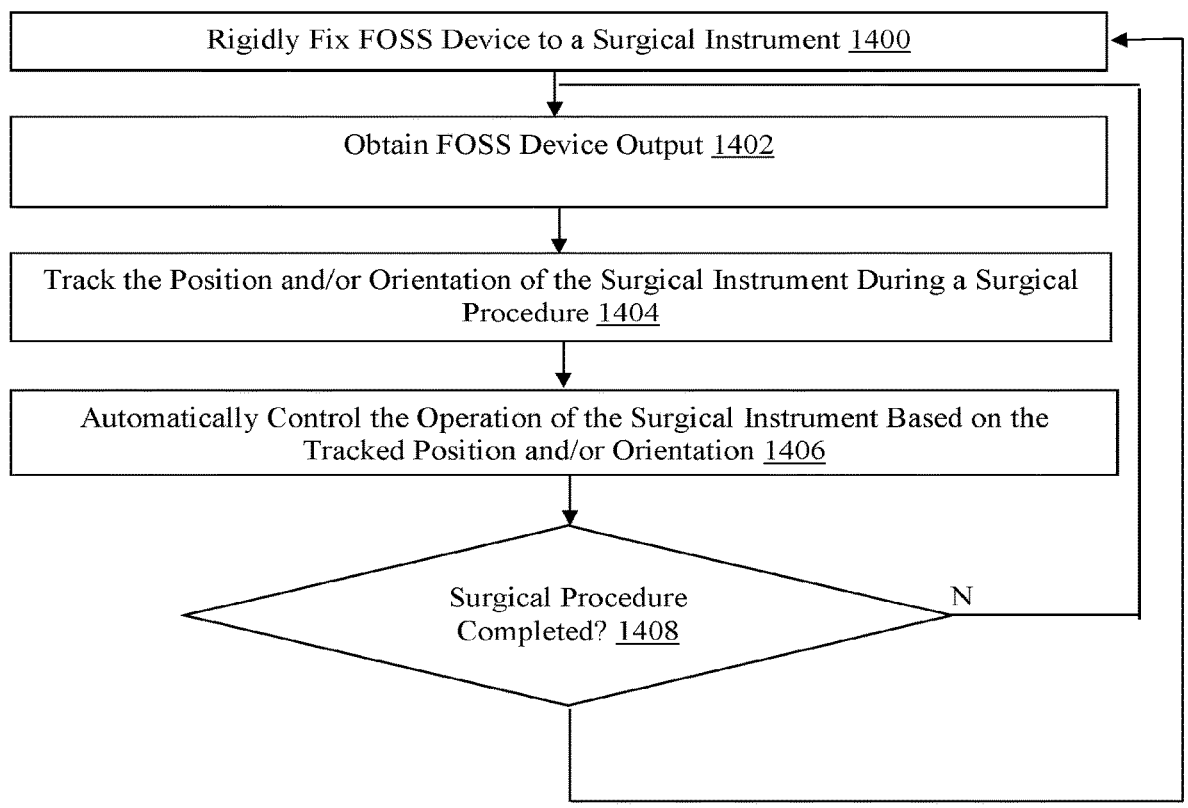
FIG. 14 depicts a flowchart of an exemplary method for tracking surgical instrument location using an exemplary FOSS device in accordance with an embodiment.

Referring more specifically to FIG. 14, a flowchart of an exemplary method for tracking surgical instrument location using the FOSS device 900 is illustrated. In this example, the tracking system 1000 is used to track surgical instrument(s) based on a location and/or orientation of a length, and/or a distal tip or other portion(s), of an optical fiber of the FOSS device 900, such as during an orthopedic and/or sports medicine surgical procedure, for example.

In step 1400 in this example, the FOSS device 900 is rigidly fixed to a surgical instrument, such as an arthroscope, shaver, robotic arm, drill, probe, and/or drill guide, for example, although the FOSS device 900 can be fixed to any other type of surgical device. The FOSS device 900 is advantageously compatible with minimally invasive procedures since the optical fiber is of relatively small diameter and can be incorporated into existing wiring for powered tools such as a scope, ablator, or shaver. Accordingly, the fixation can be based on an adhesive, integration with a cable or other portion of the instrument, and/or any other type of fixation system, and optionally can be detachable to allow for reuse.

In step 1402, the surgical tracking device 1002 obtains output from the FOSS device 900 and, optionally in a first iteration, registers the FOSS device 900, such as based on a 3D model of patient anatomy and/or a coordinate system in a surgical environment, such as an operating room. The output of the FOSS device 900 can optionally be obtained and/or registered as described and illustrated in more detail above with reference to step 1104 of FIG. 11.

In step 1404, the surgical tracking device 1002 tracks a position and/or orientation of the surgical instrument, to which the FOSS device 900 was rigidly fixed in step 1400, during a surgical procedure. In one example, the FOSS device 900 is integrated into the surgical instrument to provide live intraoperative guidance inside a patient. For example, the FOSS device 900 could be incorporated into an arthroscope used for arthroscopic procedures such that the body and/or tip location are tracked in space. In this example, the tip of the arthroscope can be known during the surgical procedure relative to the locations of the bones of the patient, for example, which can optionally also be tracked with the same or a different FOSS device 900 or another surgical tracking system.

In another example, the FOSS device 900 can be used in conjunction with a robotic arm, such as integrated within or on the limb(s) and/or joint(s) of a robotic arm such that the positions of each component of the robotic arm can be tracked in space. The tracking of the robotic arm can be used to prevent the robotic arm from colliding with other instruments or people within the surgical environment, for example, among other uses. Further, in arthroscopic procedures where robotic arm(s) are holding instrument(s) within a joint, location tracking of the robotic arm(s) and the held instrument(s), including the arthroscope, allows the surgical procedure to be performed with reduced risk of instrument collision.

Additionally, in some examples the robotic arm has seven or more degrees-of-freedom (DOF) such that there is a redundancy in DOF. Accordingly, if motion control software commands the end effector of the robotic arm to go to a certain position/orientation, there may be many ways for the robotic arm to arrive at that position/orientation, and some movements of the robotic arm will be preferable to others in order to reduce the risk of collision with other objects. Therefore, the FOSS device 900 can provide real-time feedback of the position/orientation of the robotic arm that can be fed back into the motion control software to move the robotic arm, or joints of the robotic arm away, to avoid particular areas or objects, for example.

In yet another example, the FOSS device 900 could be integrated into a drill or a drill guide. The position of the drill or drill guide could be known and/or tracked relative to the bones of a patient, for example, during a surgical procedure. In one embodiment, a guide used to drill the femoral or tibial tunnels during an anterior cruciate ligament (ACL) reconstruction may be tracked. Such an embodiment may case the difficulty of adequately accessing the medial aspect of the lateral condylar notch using an inside-out technique and a straight or curved/rigid guide to place a guidewire for the femoral tunnel.

Using a flexible guide, the surgeon may be able to better position the entry point for the guidewire. Conventionally, this results in some difficulty with respect to knowing the exact location of the entry point and the trajectory/orientation of the guidewire. However, the FOSS device 900 of this technology can advantageously be attached to the guide, including a flexible portion of the guide, such that the position and/or orientation of the tip of the guide that defines the trajectory of the guidewire can be known with increased accuracy.

With respect to soft tissues, many sports medicine procedures involve reattaching such tissues to bone or to other soft tissues. One of the challenges involved with repairing soft tissue is that it is difficult for a surgeon to determine where the device, such as a suture or an implant, will go after the device enters or passes through soft tissue. For example, in a meniscus repair, it can be difficult to see behind the meniscus when trying to repair a longitudinal or bucket handle type of tear, especially posteriorly. Given the flexible nature of the FOSS device 900 of this technology, the FOSS device can advantageously be positioned behind the meniscus and locate a tool or anatomical structure prior to deploying a suture or other implant, for example.

In step 1406, the surgical tracking device 1002 optionally automatically controls the operation of the surgical instrument to which the FOSS device 900 was rigidly fixed in step 1400 based on the position and/or orientation tracked in step 1404. As described above, the FOSS device 900 can be rigidly fixed to a guide that facilitates the drilling of the femoral tunnel during an ACL reconstruction. In this example, the position and/or orientation of the tunnel may be important to the outcome of the procedure, and the tunnel position(s) can be planned preoperatively or intraoperatively to optimally reproduce the native footprints, optimize kinematics, graft length, or on or more other parameter(s). Once the optimally planned tunnel location(s) are known relative to the individual anatomy, and the patient's bones are registered intraoperatively to the preoperative or intraoperative 3D model(s), the drill or drill guide tracked via the attached FOSS device 900 can be guided to the planned location(s).

In another embodiment, the FOSS device 900 is fixed to a shaver or burr configured to remove bone in a planned manner. For example, in femoroacetabular impingement, bony overgrowth on the pelvis or femur results in an impingement during certain activities or at certain points during the range of motion. The treatment involves shaving the overgrown bone such that the impingement during activity is resolved. Preoperative imaging via MRI or CT is often done to diagnose and determine the amount and location(s) of the impingement. A three-dimensional model of the femur and acetabulum can be created from the preoperative imaging, which can be used to simulate various activities to determine the location and/or severity of the impingement.

The impinging bone can be marked on the 3D model as bone to be removed during the procedure. Intraoperatively, the femur and/or pelvis can be tracked using individual FOSS devices 900, for example as described and illustrated in more detail above with reference to FIG. 11 or via another surgical tracking system. The shaver burr also can be tracked using the FOSS device 900, which can be incorporated into the power cable or attached to another location associated with the shaver and registered with the 3D model.

The shaver can be turned on automatically when the tip of the shaver is located in an area of the femur and/or pelvis where bone is to be removed. The shaver can also be automatically turned off or have its speed reduced when the tip of the shaver is located in an area where there is no bone to be removed and/or where bone is not to be removed. In this way, the tracking system 1000 can only remove bone where necessary or provide visual/haptic feedback to the user via the reduced shaver speed. The FOSS device 900 is used to locate the tool tip based on the tracked location and registration of the FOSS device 900 attached to the shaver. Optionally, the surgical tracking device 1002 can communicate with the surgical computer 150 to facilitate the automated control of the shaver.

Similarly, a specific amount and location of bone can be shaved in subacromial decompression or acromioplasty in shoulder arthroscopy procedures, for example, by tracking the location of the FOSS device 900 fixed to a shaver. In yet another example, soft tissue, such as damaged cartilage, meniscus, or rotator cuff can be removed using an ablator or mechanical resection device that is tracked using the FOSS device 900, for example.

In step 1408, the surgical tracking device 1002 determines whether the surgical procedure has been completed, such as based on a completion of a navigated surgical plan and/or communication from the surgical computer 150, for example, although other methods for determining that the surgical procedure has been completed can also be used. If the surgical tracking device 1002 determines that the surgical procedure has not been completed, then the No branch is taken back to step 1402, and the surgical tracking device 1002 effectively continues to track the position and/or orientation of the surgical instrument. However, if the surgical tracking device 1002 determines in step 1408 that the surgical procedure has completed, then the Yes branch is taken back to step 1400, and the FOSS device 900 or another FOSS device is rigidly fixed to the surgical instrument or another surgical instrument in another surgical procedure.

Figure 15:
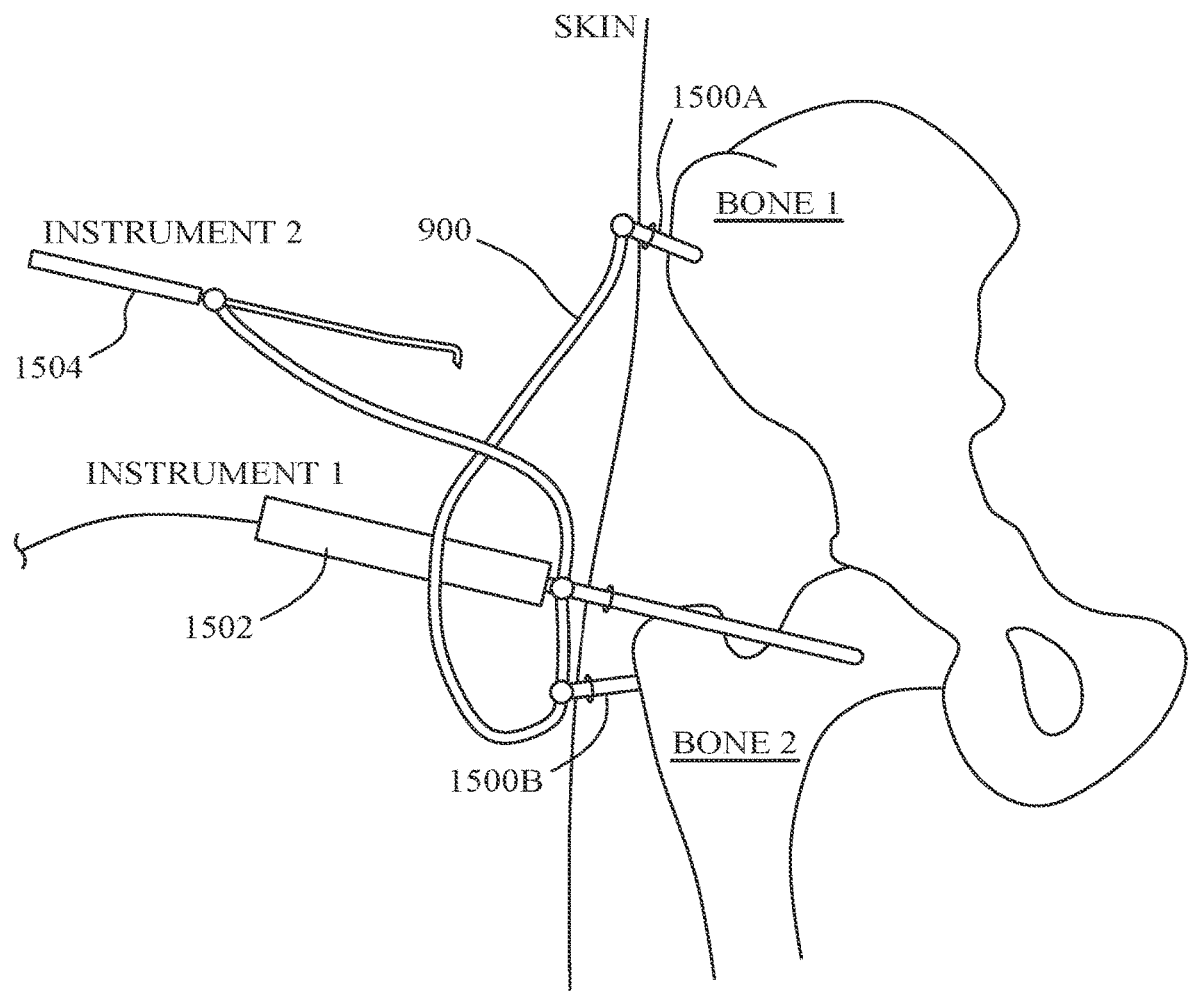
FIG. 15 depicts a deployment of an exemplary FOSS device configured to track multiple instruments and anatomical structures during the same surgical procedure in accordance with an embodiment.

While the examples described and illustrated with reference to FIGS. 11-13 relate to anatomy tracking, and the examples described and illustrated with reference to FIG. 14 relate to surgical instrument tracking, in other examples, anatomy and surgical tracking can occur simultaneously using the same FOSS device or multiple FOSS devices. Referring to FIG. 15, an exemplary deployment of the FOSS device 900 configured to track multiple instruments and anatomical structures during the same surgical procedure is illustrated. In this example, the single FOSS device 900 is strung from a rigid attachment 1500A fixed to the pelvis (illustrated as bone 1) to a rigid attachment 1500B fixed to the femur (illustrated as bone 2) to a surgical instrument 1502 to a probe 1504, thereby configured to track at least the location of the bones and instruments 1502 and 1504 with reduced hardware utilization. Other methods for tracking the location of the same or different surgical instrument(s) using the FOSS device 900 can also be used in other examples.

Surgical Instrument Flexibility Tracking

Figure 16:
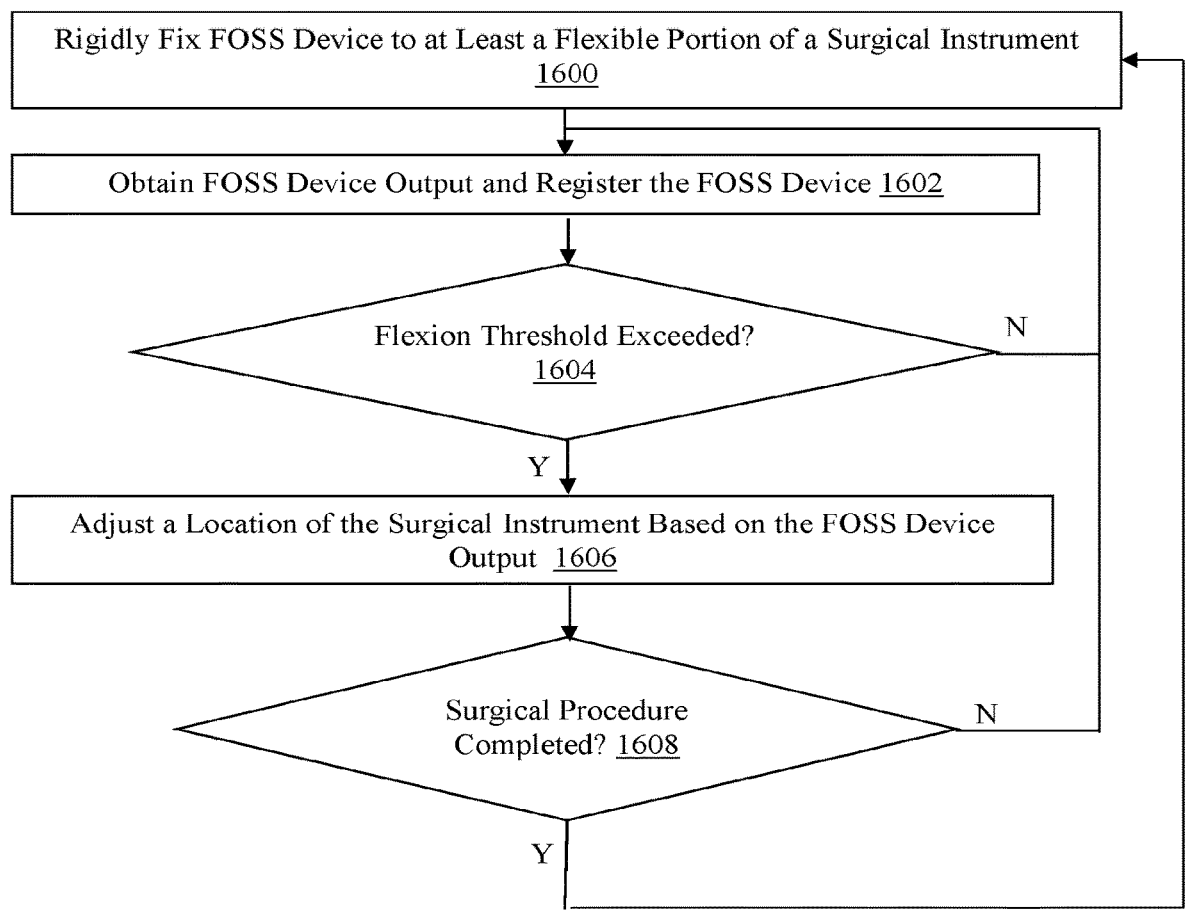
FIG. 16 depicts a flowchart of an exemplary method for tracking surgical instrument flexibility using an exemplary FOSS device in accordance with an embodiment.

Referring to FIG. 16, a flowchart of an exemplary method for tracking surgical instrument flexibility using the FOSS device 900 is illustrated. In this example, the FOSS device 900 is used to detect bending or flexion in a surgical instrument and utilize the detected flexion to control an operation and/or location of a tracked surgical instrument or a portion thereof. In this example, steps 1600, 1602, and 1608 can be performed as described and illustrated above with reference to steps 1400, 1402, and 1408 of FIG. 14, respectively. The output of the FOSS device 900 includes an indication of the strain on the sensors 902A-C, which correlates with flexion at the corresponding locations in the optical fiber of the FOSS device 900.

In step 1604, the surgical tracking device 1002 optionally determines whether a flexion threshold is exceeded. While an adjustment can be made, as described below, for every corresponding change in flexion, in this example, an optional tolerance is used that corresponds to the flexion threshold. The flexion threshold can be configurable, static, and/or dynamic, for example, and other types of thresholds can also be used. If the surgical tracking device 1002 determines that the flexion threshold has not been exceeded, then the No branch is taken back to step 1602, and the surgical tracking device 1002 continues to obtain the FOSS device output. In some embodiments, the registration of the FOSS device 900 is only performed during the first iteration. If the surgical tracking device 1002 determines that the flexion threshold has been exceeded, then the Yes branch is taken to step 1606.

In step 1606, the surgical tracking device 1002 automatically adjusts a location of the surgical instrument to which the FOSS device 900 was rigidly fixed in step 1600 based on the FOSS device output. Determining the flexion of the surgical instrument can allow a navigation computer (e.g., surgical computer 150) to digitally and automatically correct the position of the ends or specific parts (e.g., a burr tip) in 3D space, which can mitigate the need to structurally stiffen the instrument or portion(s) thereof.

In one particular example, a shaver has a burr that is used to remove soft tissue or bone during an arthroscopic procedure and a shaft that is designed to limit the flexibility of the burr tip relative to the body. Despite this design, due at least in part to the materials used, some inherent flexibility remains in the burr such that the tip of the burr may not be collinear with the shaft and the body of the shaver throughout the arthroscopic procedure. When using computer assisted surgery and navigating or controlling an instrument based on its position, it is important to accurately determine the location and orientation of the active portion or end effector of the instrument. In this example in which the active portion is a burr tip with some flexibility, using the FOSS device 900 as attached to the shaft of the shaver, for example, can advantageously facilitate tracking of the tip of the burr with increased accuracy.

In another example, the need to detect an intermediate hub of a surgical instrument and then correct for bending of an associated shaft could be simplified with this technology by eliminating the sensing of the intermediate hub. For example, a single FOSS device 900 could be fixed to a known position and then extended to an arthroscope's hub and along the arthroscope to its distal end and its associated direction of view. The flexibility of other types of instruments could also be detected in other examples.

Accordingly, as described and illustrated by way of the examples herein, this technology advantageously facilitates patient anatomy and surgical instrument location tracking without requiring line-of-sight as in other optical tracking systems. Additionally, the FOSS device 900 of this technology does not have any issues with metal interference causing distortion within the tracking field, as can occur with electromagnetic tracking systems. The optical fiber of the FOSS device 900 also can be flexible, thereby allowing a relatively wide operative field. Because the optical fiber of the FOSS device 900 can be tracked along its entire length, a single FOSS device can be used to track multiple structures if fixed to those structures. Further, the flexibility of the FOSS device 900 also advantageously facilitates tracking in areas where flexible guides may be required. Accordingly, this technology significantly improves surgical tracking and computer navigated surgical systems as well as associated patient outcomes.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

We claim:

1. A method for surgical instrument location tracking, the method comprising:
    generating strain data using a shape sensor attached to a surgical instrument, the shape sensor comprising a plurality of distributed strain sensors along a length of the shape sensor;
    determining, from the strain data generated by the plurality of distributed strain sensors of the shape sensor, a shape of the shape sensor;
    tracking location of a distal end of the surgical instrument based on the shape of the shape sensor, wherein the tracking results in a tracked location; and
    adjusting a graphical display to output a representation of at least a portion of the surgical instrument based on the tracked location,
    wherein the surgical instrument comprises a flexible portion of a drill guide, and wherein the method further comprises placing a guidewire for a femoral tunnel based on the tracked location in order to define one or more of a trajectory or an orientation of the guidewire.

2. The method of claim 1 wherein attaching the shape sensing device comprises attaching a fiber optic shape sensing (FOSS) device, wherein the FOSS device comprises the distributed strain sensors in the form of an optical fiber comprising fiber Bragg grating (FBG) sensors.

3. The method of claim 2 wherein determining the shape of the shape sensor comprises:
    introducing broadband light into the optical fiber of the FOSS device; and
    generating reflectivity data based on reflection from the FBG sensors of the broadband light.

4. The method of claim 2, further comprising controlling a location or an operation of the surgical instrument based on the tracked location of the FBG sensors.

5. The method of claim 1, further comprising controlling an operation of the surgical instrument based on the tracked location.

6. The method of claim 1, wherein the surgical instrument comprises two or more surgical instruments attached to the shape sensor.

7. A method for surgical instrument location tracking, the method comprising:
    generating strain data using a shape sensor attached to a surgical instrument, the shape sensor comprising a plurality of distributed strain sensors along a length of the shape sensor;
    determining, from the strain data generated by the plurality of distributed strain sensors of the shape sensor, a shape of the shape sensor;
    tracking location of a distal end of the surgical instrument based on the shape of the shape sensor, wherein the tracking results in a tracked location;
    adjusting a graphical display to output a representation of at least a portion of the surgical instrument based on the tracked location, wherein the surgical instrument comprises a limb or joint of a robotic arm;
    determining when a collision of the limb or joint of the robotic arm, or an instrument held by the robotic arm, with another tracked object in a surgical environment is imminent based on the tracked location; and
    preventing the collision based on control of the location of the limb or joint of the robotic arm.

8. A method for surgical instrument location tracking, the method comprising:
    generating strain data using a shape sensor attached to a surgical instrument, the shape sensor comprising a plurality of distributed strain sensors along a length of the shape sensor;
    determining, from the strain data generated by the plurality of distributed strain sensors of the shape sensor, a shape of the shape sensor;
    tracking location of a distal end of the surgical instrument based on the shape of the shape sensor, wherein the tracking results in a tracked location; and
    adjusting a graphical display to output a representation of at least a portion of the surgical instrument based on the tracked location,
    wherein the surgical instrument comprises a shaver, and the method further comprises automatically controlling the shaver based on the tracked location to remove one or more portions of an anatomical structure of a patient.

9. A method for surgical instrument location tracking, the method comprising:
    generating strain data using a shape sensor attached to a surgical instrument, the shape sensor comprising a plurality of distributed strain sensors along a length of the shape sensor;
    determining, from the strain data generated by the plurality of distributed strain sensors of the shape sensor, a shape of the shape sensor;
    tracking location of a distal end of the surgical instrument based on the shape of the shape sensor, wherein the tracking results in a tracked location; and
    adjusting a graphical display to output a representation of at least a portion of the surgical instrument based on the tracked location,
    wherein the surgical instrument comprises an ablator, and the method further comprises automatically controlling the ablator based on the tracked location to remove one or more portions of an anatomical structure of a patient.

10. A method for anatomical structure location tracking, the method comprising:
    attaching a shape sensor to the anatomical structure of a patient;

generating strain data using the shape sensor attached to the anatomical structure, the shape sensor comprising a plurality of distributed strain sensors along a length of the shape sensor;

determining, from the strain data generated by the plurality of distributed strain sensors of the shape sensor, a shape of the shape sensor;

tracking a location of the anatomical structure based on the shape of the shape sensor, wherein the tracking results in a tracked location; and adjusting a graphical display to output a representation of at least a portion of the anatomical structure based on the tracked location.

11. A surgical tracking system comprising:

a surgical instrument;

a shape sensor comprising a plurality of distributed strain sensors along a length of the shape sensor, the shape sensor coupled to the surgical instrument;

a surgical tracking device coupled to the shape sensor, the surgical tracking device comprising:

a processor;

a memory coupled to the processor; and a display device coupled to the processor;

the memory storing instructions that, when executed by the processor, cause the processor to:

generate strain data from the plurality of distributed strain sensors;

determine, from strain data, a shape of the shape sensor;

track a location of the surgical instrument based on the shape of the shape sensor, wherein the tracking results in a tracked location; and adjust the display device to output a representation of at least a portion of the surgical instrument based on the tracked location, wherein the surgical instrument comprises at least one of a flexible portion of a drill guide, a shaver, and an ablator.

12. The surgical tracking system of claim 11, wherein the shape sensing device comprises a fiber optic shape sensing (FOSS) device, wherein the FOSS device comprises the distributed strain sensors in the form of an optical fiber comprising fiber Bragg grating (FBG) sensors.

13. The surgical tracking system of claim 12, wherein when the processor determines the shape, the instructions cause the processor to:

introduce broadband light into the optical fiber of the FOSS device; and generate reflectivity data based on reflection from the FBG sensors of the broadband light.

14. The surgical tracking system of claim 11, wherein the instructions further cause the processor to control an operation of the surgical instrument based on the tracked location.

15. The surgical tracking system of claim 11, wherein the surgical instrument comprises two or more surgical instruments attached to the shape sensor.

16. A surgical tracking system, comprising:

a shape sensor comprising a plurality of distributed strain sensors along a length of the shape sensor, wherein the shape sensor is attached an anatomical structure of a patient;

a surgical tracking device coupled to the shape sensor, the surgical tracking device comprising:

a processor;

a memory coupled to the processor; and a display device coupled to the processor;

the memory storing instructions that, when executed by the processor, cause the processor to:

generate strain data from the plurality of distributed strain sensors;

determine, from strain data, a shape of the shape sensor;

track a location of the anatomical structure based on the shape of the shape sensor, wherein the tracking results in a tracked location; and adjust the display device to output a representation of at least a portion of the anatomical structure based on the tracked location.

* * * * *